US010815298B2

(12) United States Patent
Baumert et al.

(10) Patent No.: US 10,815,298 B2
(45) Date of Patent: Oct. 27, 2020

(54) ANTI-CLAUDIN 1 MONOCLONAL ANTIBODIES FOR THE PREVENTION AND TREATMENT OF HEPATOCELLULAR CARCINOMA

(71) Applicants: INSTITUT HOSPITALIER UNIVERSITAIRE DE STRASBOURG, Strasbourg (FR); INSERM (INSTITUT NATIONAL DE LA SANTE ET DE LA RECHERCHE MEDICALE), Paris (FR); UNIVERSITE DE STRASBOURG, Strasbourg (FR)

(72) Inventors: Thomas Baumert, Freiburg (DE); Eric Robinet, Colmar (FR); Mirjam Zeisel, Strasbourg (FR)

(73) Assignees: Institut Hospitalier Universitaire de Strasbourg, Strasbourg (FR); Institut National de la Sante et de la Recherche Medicale, Paris (FR); Universite de Strasbourg, Strasbourg (FR)

( * ) Notice: Subject to any disclaimer, the term of this patent is extended or adjusted under 35 U.S.C. 154(b) by 131 days.

(21) Appl. No.: 15/557,969

(22) PCT Filed: Mar. 18, 2016

(86) PCT No.: PCT/EP2016/055942
§ 371 (c)(1),
(2) Date: Sep. 13, 2017

(87) PCT Pub. No.: WO2016/146809
PCT Pub. Date: Sep. 22, 2016

(65) Prior Publication Data
US 2018/0057587 A1 Mar. 1, 2018

(30) Foreign Application Priority Data
Mar. 19, 2015 (EP) .................................... 15159872

(51) Int. Cl.
A61K 39/395 (2006.01)
C07K 16/28 (2006.01)
C07K 16/30 (2006.01)
A61K 45/06 (2006.01)

(52) U.S. Cl.
CPC ........ *C07K 16/28* (2013.01); *A61K 39/39558* (2013.01); *A61K 45/06* (2013.01); *C07K 2317/76* (2013.01)

(58) Field of Classification Search
None
See application file for complete search history.

(56) References Cited

U.S. PATENT DOCUMENTS 8,518,408 B2 * 8/2013 Baumert ................ C07K 16/28
424/149.1
2016/0158380 A1 6/2016 Del Rio et al.

FOREIGN PATENT DOCUMENTS

| WO | WO 2010/034812 | * | 4/2010 |
| WO | 2015/014657 |  | 2/2015 |
| WO | WO 2015/014657 | * | 2/2015 |

OTHER PUBLICATIONS

International Search Report and Written Opinion of the International Searching Authority dated May 27, 2016, which issued during prosecution of International Application No. PCT/EP2016/055942.

* cited by examiner

*Primary Examiner* — Laura B Goddard
(74) *Attorney, Agent, or Firm* — Morgan, Lewis & Bockius LLP

(57) ABSTRACT

Use of anti-Claudin 1 monoclonal antibodies and pharmaceutical compositions thereof, for the prevention and/or treatment of hepatocellular carcinoma in patients suffering from liver disease, in particular liver disease that is not associated with HCV infection or in patients who have been cured from HCV infection. Methods of preventing and/or treating hepatocellular carcinoma by administration of such a monoclonal antibody, or a pharmaceutical composition thereof, are also described. Experimental results with the hepatocarcinoma cell line HuH-7.5.1 are given.

6 Claims, 16 Drawing Sheets

A

B

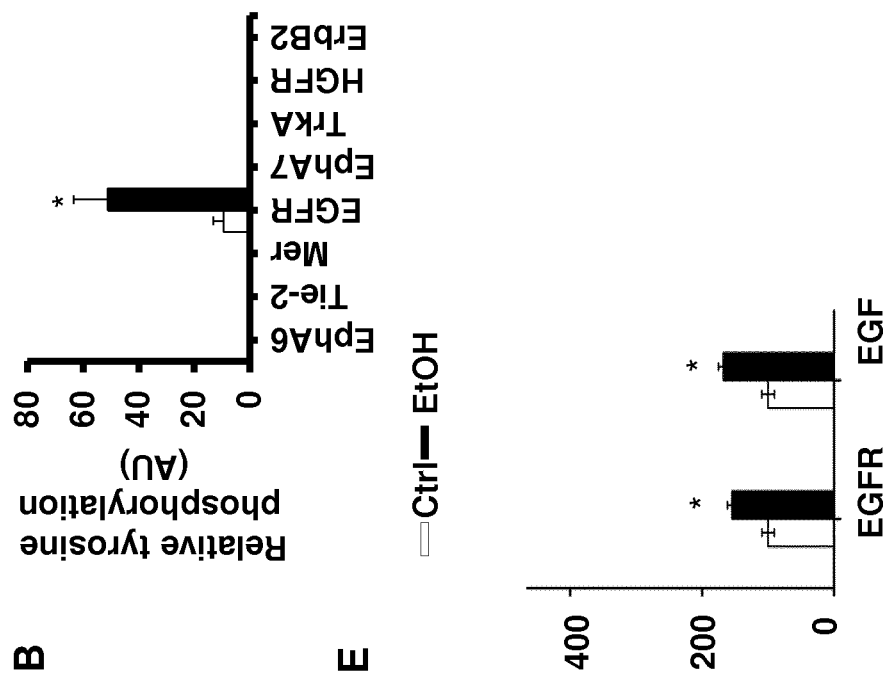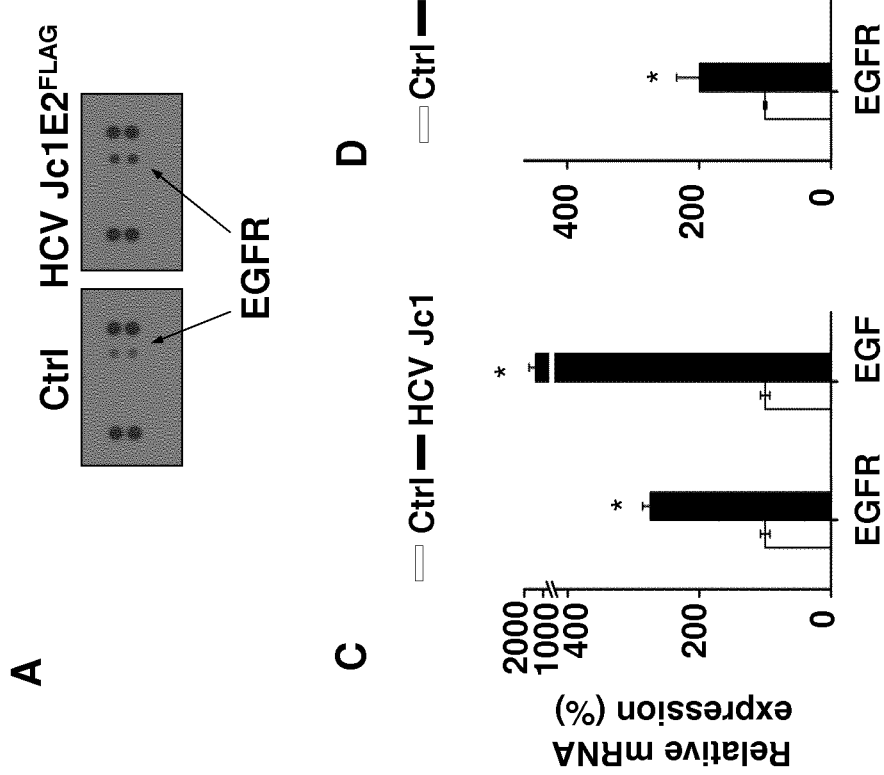
FIG. 3A FIG. 3B FIG. 3C FIG. 3D FIG. 3E

B Suppression of MAPK-signaling related gene expression

A Suppression of EGFR signaling pathways

A

B

C

A

B

A

B

C

FIG. 11A
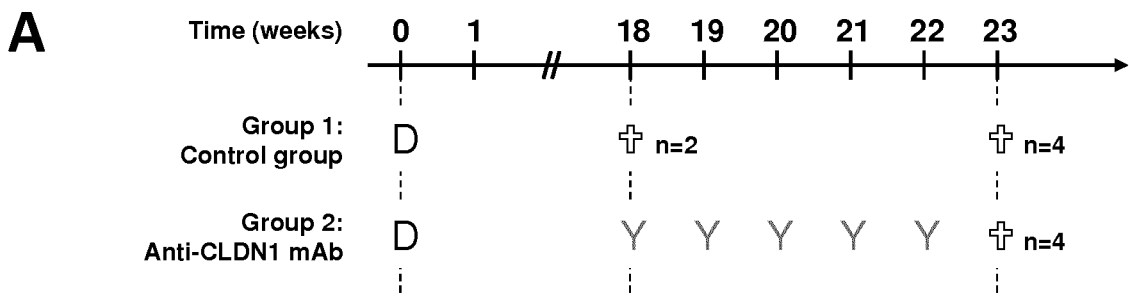
FIG. 11B
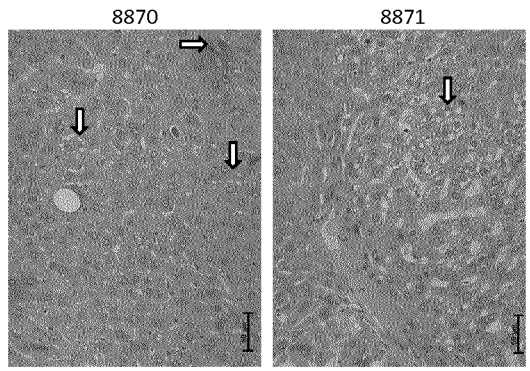
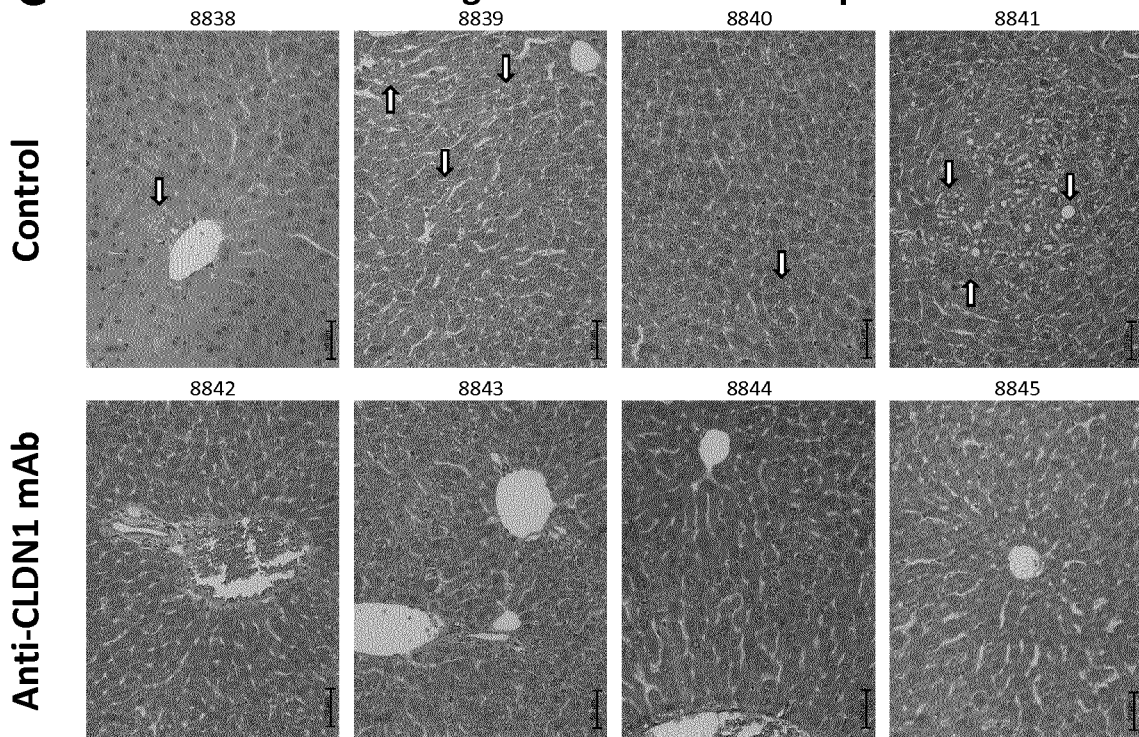
FIG. 11C

E

Liver tumor in control group (mouse #8841)

ANTI-CLAUDIN 1 MONOCLONAL ANTIBODIES FOR THE PREVENTION AND TREATMENT OF HEPATOCELLULAR CARCINOMA

RELATED PATENT APPLICATIONS

The present application is filed pursuant to 35 U.S.C. § 371 as a U.S. National Phase Application of International Patent Application No. PCT/EP2016/055942, which was filed on Mar. 18, 2016, claiming the benefit of priority to European Patent Application number EP 15 159 872.9, which was filed on Mar. 19, 2015. The entire contents of each of the aforementioned patent applications is incorporated herein by reference in its entirety.

BACKGROUND OF THE INVENTION

Hepatocellular carcinoma (HCC) is the second leading and fastest rising cause of cancer death worldwide (International Agency for Research on Cancer; GLOBOCAN 2012: Estimated Cancer Incidence, Mortality and Prevalence Worldwide in 2012—webpage: globocan.iarc.fr). HCC accounts for more than 500,000 new cases per year and nearly as many deaths due to poor disease prognosis. Chronic hepatitis C virus (HCV) infection is the most important risk factor for developing liver cirrhosis and HCC (El-Serag, N Engl J Med., 2011, 365(12): 1118-1127). It is estimated that approximately 3% of the world population is chronically infected with HCV (World Health Organization). Other major risk factors for HCC include infection with hepatitis B virus (HBV), alcoholic liver disease, and non-alcoholic fatty liver disease. Less common causes include hereditary hemochromatosis, alpha 1-antitrypsin deficiency, auto-immune hepatitis, some porphyrias, Wilson's disease, aflatoxin exposure. The distribution of these risk factors among patients with HCC is highly variable, depending on geographic region, and on race or ethnic group. Most of these risk factors lead to the formation and progression of cirrhosis, which is present in 80 to 90% of patients with HCC. The 5-year cumulative risk for the development of HCC in patients with cirrhosis ranges between 5% and 30%, depending on the cause, region or ethnic group, and stage of cirrhosis. In 2011, end-stage liver disease and HCC resulted in 6,342 liver transplants associated with costs of more than 1 billion US dollars for the procedure alone (see NIH webpage: optn.transplant.hrsa-.gov/latestData/step2.asp).

Although HCC may be avoided by addressing the underlying cause in the early stage of the disease, strategies to prevent HCC in patients with established cirrhosis and advanced fibrosis, in which the risk of HCC persists despite treatment of the underlying cause, are lacking. Indeed, even curing HCV infection does not eliminate the risk of HCC development when advanced fibrosis is already present (van der Meer et al., JAMA, 2012, 308(24): 2584-2593). Currently, curative treatment options for patients with cirrhotic HCC are mainly limited to liver transplantation, an impractical, invasive and resource-intensive solution. Given the extremely frequent tumor recurrence after surgical treatment and absence of efficient medical treatment strategies, prevention of HCC development in patients with advanced liver fibrosis is considered to be the most effective strategy to substantially impact on patient survival (Hoshida et al., J Hepatol., 2014, 61(1S): S79-S90; Hoshida et al., Curr Cancer Drug Targets, 2012, 12(9):1129-1159).

In light of the increasing economic burden of patients with cirrhosis and associated HCC, novel strategies to prevent and treat HCC in patients with advanced liver disease are therefore urgently needed.

SUMMARY OF THE INVENTION

The present invention relates to systems and strategies for the prevention and/or treatment of hepatocellular carcinoma (HCC) irrespective of the etiology. In particular the present invention is directed to the use of anti-Claudin-1 antibodies for preventing and/or treating hepatocellular carcinoma, including hepatocellular carcinoma that is not associated with HCV infection and hepatocellular carcinoma that has developed, or that is susceptible of developing, after HCV infection has been cured. Analyzing virus-induced cell signalling and a 186-liver gene signature which predicts HCC risk in cirrhotic patients of various etiologies, the present Applicants have shown that an anti-Claudin 1 monoclonal antibody, which they had previously developed and shown to cure chronic HCV infection without detectable adverse effects (EP 08 305 597 and WO 2010/034812), interferes with liver cell signalling and reverses a patient-derived HCC risk signature in a liver cell-based model system. Modulation of signalling and transcriptional reprogramming was found to be independent of the antiviral activity of the antibody, indicating that the anti-Claudin 1 monoclonal antibody acts directly onto oncogenic pathways. Indeed, performing mechanistic studies, the Applicants have demonstrated that the antibody impairs the EGFR-MAPK signalling pathway and expression of inflammatory response genes, which have been suggested as drivers for hepatocarcinogenesis. Compared to antiviral agents and other candidate compounds for HCC chemoprotection, the anti-Claudin 1 monoclonal antibody was the most potent to reverse the HCC high-risk signature.

Consequently, in one aspect, the present invention provides an anti-Claudin 1 antibody, or a biologically active fragment thereof, for use in the prevention or treatment of a non-HCV-associated hepatocellular carcinoma in a subject, i.e., in a subject that has never been infected with HCV or in a subject that has been cured from HCV infection.

In certain embodiments, the non-HCV associated hepatocellular carcinoma is associated with hepatitis B virus (HBV) infection, alcoholism, non-alcoholic fatty liver disease (NAFLD), hereditary hemochromatosis, alpha 1 antitrypsin deficiency, *porphyria cutanea tarda*, Wilson's disease, tyrosinemia, glycogen storage diseases, autoimmune hepatitis, primary biliary cirrhosis, or exposure to aflatoxins. In other embodiments, the non-HCV-associated hepatocellular carcinoma is hepatocellular carcinoma of unknown origin.

In certain embodiments, the anti-Claudin 1 antibody is a polyclonal antibody. In other embodiments, the anti-Claudin 1 antibody is a monoclonal antibody.

In certain embodiments, the anti-Claudin 1 antibody is a monoclonal antibody secreted by a hybridoma cell line co-deposited by INSERM and GENOVAC at the DSMZ on Jul. 29, 2008 under an Accession Number selected from the group consisting of DSM ACC2931, DSM ACC2932, DSM ACC2933, DSM ACC2934, DSM ACC2935, DSM ACC2936, DSM ACC2937, and DSM ACC2938. In other embodiments, the anti-Claudin 1 antibody comprises the six complementary determining regions (CDRs) of a monoclonal antibody secreted by a hybridoma cell line co-deposited by INSERM and GENOVAC at the DSMZ on Jul. 29, 2008 under an Accession Number selected from the group consisting of DSM ACC2931, DSM ACC2932, DSM ACC2933, DSM ACC2934, DSM ACC2935, DSM ACC2936, DSM ACC2937, and DSM ACC2938.

In certain embodiments, the anti-Claudin 1 antibody is humanized, de-immunized or chimeric.

A biologically active fragment of an anti-Claudin 1 antibody is a fragment that retains the biological property of the antibody to interfere with liver cell signalling and to reverse a patient-derived HCC risk signature.

More generally, the present invention encompasses the use of any molecule that comprises an anti-Claudin-1 antibody, or a biologically active fragment thereof, including chimeric antibodies, humanized antibodies, de-immunized antibodies and antibody-derived molecules comprising at least one complementary determining region (CDR) from either a heavy chain or light chain variable region of an anti-Claudin-1 monoclonal antibody secreted by a hybridoma cell line, including molecules such as Fab fragments, F(ab')$_2$ fragments, Fd fragments, Sc antibodies (single chain antibodies), diabodies, individual antibody light single chains, individual antibody heavy chains, chimeric fusions between antibody chains and other molecules, and antibody conjugates, such as antibodies conjugated to a diagnostic agent (detectable moiety) or therapeutic agent, so long as these antibody-related molecules retain the biological property to interfere with liver cell signalling and/or to reverse a patient-derived HCC risk signature and/or to prevent or treat non-HCV-associated hepatocellular carcinoma.

In a related aspect, the present invention provides a method for preventing hepatocellular carcinoma in a subject suffering from a non-HCV-associated liver disease, said method comprising a step of administering to the subject in need thereof an effective amount of an anti-Claudin 1 antibody or a biologically active fragment thereof. As indicated above, the subject suffering from liver disease has never been infected with HCV or has been cured from HCV infection.

In certain embodiments, the underlying cause of the non-HCV associated liver disease is selected from the group consisting of hepatitis B virus (HBV) infection, alcoholism, non-alcoholic fatty liver disease (NAFLD), hereditary hemochromatosis, alpha 1 antitrypsin deficiency, *porphyria* cutanea *tarda*, Wilson's disease, tyrosinemia, glycogen storage diseases, autoimmune hepatitis, primary biliary cirrhosis, and exposure to aflatoxins. In other embodiments, the non-HCV-associated liver disease is of unknown origin.

In another related aspect, the present invention provides a method of treating non-HCV-associated hepatocellular carcinoma in a subject, said method comprising a step of administering to the subject in need thereof an effective amount of an anti-Claudin 1 antibody or a biologically active fragment thereof. As indicated above, the subject suffering from hepatocellular carcinoma has never been infected with HCV or has been cured from HCV infection.

In certain embodiments, the non-HCV-associated hepatocellular carcinoma carcinoma is associated with hepatitis B virus (HVB) infection, alcoholism, non-alcoholic fatty liver disease (NAFLD), hereditary hemochromatosis, alpha 1 antitrypsin deficiency, *porphyria* cutanea *tarda*, Wilson's disease, tyrosinemia, glycogen storage diseases, autoimmune hepatitis, primary biliary cirrhosis, or exposure to aflatoxins. In other embodiments, the non-HCV-associated hepatocellular carcinoma is hepatocellular carcinoma of unknown origin.

The anti-Claudin 1 antibodies and biologically active fragments thereof that may be used in the practice of the method of prevention of the present invention and in the method of treatment of the present invention are as described above.

In another aspect, the present invention provides a pharmaceutical composition comprising an effective amount of an anti-Claudin 1 antibody, or a biologically active fragment thereof, and at least one pharmaceutically acceptable carrier or excipient, for use in the prevention or treatment of a non-HCV associated hepatocellular carcinoma in a subject, i.e., a subject that has never been infected with HCV or in as subject that has been cured from HCV infection.

In certain embodiments, the non-HCV associated hepatocellular carcinoma is associated with hepatitis B virus infection, alcoholism, non-alcoholic fatty liver disease (NAFLD), hereditary hemochromatosis, alpha 1 antitrypsin deficiency, *porphyria* cutanea *tarda*, Wilson's disease, tyrosinemia, glycogen storage diseases, autoimmune hepatitis, primary biliary cirrhosis, or exposure to aflatoxins. In other embodiments, the non-HCV-associated hepatocellular carcinoma is hepatocellular carcinoma of unknown origin.

The anti-Claudin 1 antibodies and biologically active fragments thereof that may be present in a pharmaceutical composition according to the present invention are as described above.

In certain embodiments, a pharmaceutical composition according to present invention further comprises an additional therapeutic agent. The additional therapeutic agent may be is selected from the group consisting of anti-viral agents, anti-inflammatory agents, immunomodulatory agents, analgesics, antimicrobial agents, antibacterial agents, antibiotics, antioxidants, antiseptic agents, anti-cancer agents and combinations thereof.

In a related aspect, the present invention provides an anti-Claudin 1 antibody, or a biologically active fragment thereof, for the manufacture of a medicament for the prevention and/or treatment of non-HCV-associated hepatocellular carcinoma in a subject.

These and other objects, advantages and features of the present invention will become apparent to those of ordinary skill in the art having read the following detailed description of the preferred embodiments.

BRIEF DESCRIPTION OF THE DRAWING

FIG. 3A-G. CLDN1-specific mAb impairs EGFR/MAPK signaling and expression in human liver cells. A, B. Huh7.5.1 cells were infected with HCV Jc1 and harvested for proteomic analyses. Infection with HCV Jc1-E2$^{FLAG}$ results in increased EGFR phosphorylation. A. Receptor tyrosine kinase (RTK) phosphorylation was assessed in cell lysates using the Human Phospho-RTK Array Kit (R&D Systems). B. Quantification of dot blot intensities of phosphorylated proteins using Image J software. Mean±SEM of integrated dot blot densities, n=3. C-E. EGFR and EGF mRNA expression (relative to GAPDH mRNA) in uninfected (Ctrl) and HCV Jc1-infected Huh7.5.1$^{dif}$ cells (C; n=9); uninfected (Ctrl) and HBV-infected HepG2-NTCP cells (D; n=12); Huh7.5.1$^{dif}$ cells incubated in absence (Ctrl) or presence of 40 mM ethanol (E; n=6). Mean percentage±SEM is shown. * Mann-Whitney U-test (p-value <0.01). F. CLDN1-specific mAb impairs HCV-induced host cell signaling. Detection of kinase phosphorylation in chronically HCV Jc1-infected Huh7.5.1 cells treated with control or CLDN1-specific mAbs (100 μg/mL; 24 h) using human phosphokinase arrays. p-Erk1/2 highlighted by black squares in F was quantified using Image J software (NIH). Results are shown as mean±SEM of integrated dot blot densities from 2 independent experiments performed in duplicate. G. Reversal of EGFR-MAPK signal pathway expression by CLDN1-specific mAb treatment. Huh7.5.1$^{d1f}$ cells were HCV Jc1 infected. Total RNA was isolated and subjected to NanoString analysis. Plots represent GSEA enrichment scores of EGFR signaling in cancer retrieved from oncogenic signatures database (EGFR_UP.V1_UP).

FIG. 11A-E. Prevention and treatment of liver disease by CLDN1 specific mAb in a DEN mouse model for liver disease and HCC. A. Approach used. C3H/He mice (n=10) received a single injection of DEN (D on the graph). Eighteen weeks post DEN injection and before treatment with antibody, two mice were sacrificed for baseline analyses (✞). From week 18 until week 23, the remaining 8 mice were subjected to treatment with mouse CLDN1-specific Ab mIgG3 (Y) (n=4; treatment group) or not treated (n=4; control group). One week after the last antibody treatment, livers were harvested for post-treatment analyses (✞). Liver tissue was fixed and stained with either hematoxillin/eosin (B, C, E) or Masson's trichrome (D). B. Liver disease at baseline prior to antibody treatment. Eighteen weeks post DEN injection and before treatment with antibody, two mice were sacrificed. Livers of mice were harvested, fixed and stained with hematoxillin/eosin. Arrows show focal areas of steatosis in the liver of all mice. Magnification ×200. C, D and E. Liver disease post treatment with CLDN1-specific mAb. C. Livers were harvested post treatment at week 23 and stained with hematoxillin/eosin. Arrows show areas of steatosis exclusively in control mice but not in anti-CLDN1 treated mice. Magnification ×200. D. Masson's trichrome staining of the livers of two out of four mice per group, confirming the presence of steatosis (arrows) in control mice while steatosis is not or barely detectable in mice treated with CLDN1-specific mAb. Two magnifications (×50 and ×200) are shown. E. Hematoxillin/eosin staining of a liver tumor in a mouse of the control group at two different magnifications (×50 and ×200). No tumors were detected in CLDN1-specific antibody treated mice. Images are representative of the entire liver. Identification numbers of the mice are indicated on each slide (D-E). Size bars: 200 µm for ×50 magnification and 50 µm for ×200 magnification.

DEFINITIONS

Figure 1A:
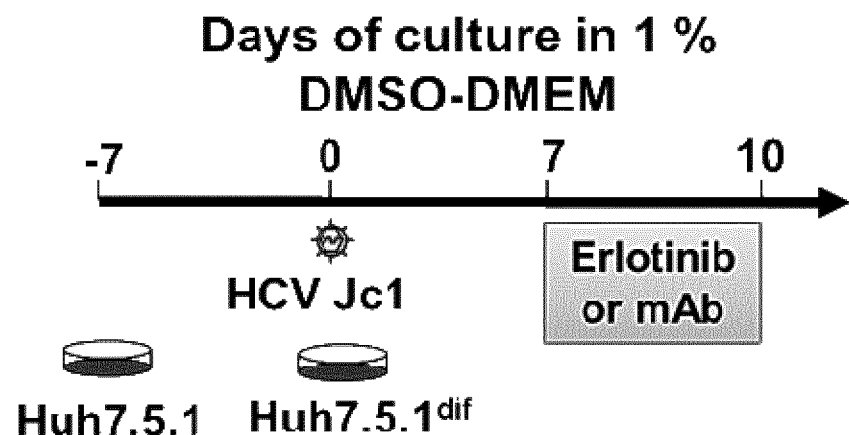
FIG. 1A-C. Persistent HCV infection-induced HCC 186-gene signature is reversed following CLDN1-specific mAb treatment in Huh7.5.1$^{dif}$ cells. A. Huh7.5.1 cells were differentiated into hepatocyte-like Huh7.5.1$^{dif}$ cells, persistently infected using HCV Jc1 and subjected to erlotinib or CLDN1-specific mAb treatment or no treatment on day 7 post-infection, then subjected to transcriptomics analysis. B. Immunodetection of HCV E2 protein (day 7 of infection). Dapi of nuclei staining in blue. Scale bar 50 µm. C. GSEA showing the reversal of the HCC high- and low-risk genes following erlotinib and CLDN1-specific mAb treatment. Compared to erlotinib, CLDN1 mAb showed better efficacy in reversing the HCC high risk profile.

Throughout the specification, several terms are employed that are defined in the following paragraphs.

As used herein, the term "subject" refers to a human or another mammal (e.g., primate, dog, cat, goat, horse, pig, mouse, rat, rabbit, and the like), that can develop hepatocellular carcinoma, but may or may not be suffering from the disease. Non-human subjects may be transgenic or otherwise modified animals. In many embodiments of the present invention, the subject is a human being. In such embodiments, the subject is often referred to as an "individual" or a "patient" The term "individual" does not denote a particular age, and thus encompasses newborns, children, teenagers, and adults. The term "patient" more specifically refers to an individual suffering from a disease. In the practice of the present invention, a patient will generally be diagnosed with a liver disease.

The term "treatment" is used herein to characterize a method or process that is aimed at (1) delaying or preventing the onset of a disease or condition (e.g., hepatocellular carcinoma); (2) slowing down or stopping the progression, aggravation, or deterioration of the symptoms of the disease or condition (e.g., liver disease); (3) bringing about amelioration of the symptoms of the disease or condition; or (4) curing the disease or condition. A treatment may be administered prior to the onset of the disease or condition, for a prophylactic or preventive action. Alternatively or additionally, a treatment may be administered after initiation of the disease or condition, for a therapeutic action.

The terms "hepatocellular carcinoma" and "HCC" are used herein interchangeably. They refer to the most common type of liver cancer, also called malignant hepatoma. As used herein, the terms "HCV-associated hepatocellular carcinoma" and HCV-associated liver disease" refers to hepatocellular carcinoma and liver disease respectively that are secondary to infection with hepatitis C virus (HCV). As used herein, the term "non-HCV-associated hepatocellular carcinoma" refers to hepatocellular carcinoma that develops, or that is susceptible of developing, in a patient who has never been infected with HCV. "Non-HCV-associated hepatocellular carcinoma" also includes hepatocellular carcinoma that develops, or that is susceptible of developing, in a patient who has been cured from HCV infection. Similarly, the term "non-HCV-associated liver disease" refers to a liver disease that has developed in a patient who has never been infected with HCV or in patient who has been cured from HCV infection. Examples of non-HCV-associated hepatocellular carcinoma/liver disease include hepatocellular carcinoma/liver disease secondary to hepatitis B virus (HBV) infection, alcoholic liver disease, non-alcoholic fatty liver disease, hereditary hemochromatosis, alpha 1-antitrypsin deficiency, auto-immune hepatitis, some porphyrias, Wilson's disease, aflatoxin exposure, type 2 diabetes, obesity, etc . . . , as well as hepatocellular carcinoma/liver disease of unknown origin.

A "pharmaceutical composition" is defined herein as comprising an effective amount of at least one anti-Claudin 1 antibody (or a biologically active fragment thereof), and at least one pharmaceutically acceptable carrier or excipient.

As used herein, the term "effective amount" refers to any amount of a compound, agent, antibody, or composition that is sufficient to fulfil its intended purpose(s), e.g., a desired biological or medicinal response in a cell, tissue, system or subject. For example, in certain embodiments of the present invention, the purpose(s) may be: to prevent the onset of hepatocellular carcinoma, to slow down, alleviate or stop the progression, aggravation or deterioration of the symptoms of liver disease or hepatocellular carcinoma; to bring about amelioration of the symptoms of the disease, or to cure the hepatocellular carcinoma.

The term "pharmaceutically acceptable carrier or excipient" refers to a carrier medium which does not interfere with the effectiveness of the biological activity of the active ingredient(s) and which is not excessively toxic to the host at the concentration at which it is administered. The term includes solvents, dispersion, media, coatings, antibacterial and antifungal agents, isotonic agents, and adsorption delaying agents, and the like. The use of such media and agents for pharmaceutically active substances is well known in the art (see for example "*Remington's Pharmaceutical Sci-*

*ences"*, E.W. Martin, 18th Ed., 1990, Mack Publishing Co.: Easton, Pa., which is incorporated herein by reference in its entirety).

The term "human Claudin-1 or human CLDN1" refers to a protein having the sequence shown in NCBI Accession Number NP 066924, or any naturally occurring variants commonly found in HCV permissive human populations. The term "extracellular domain" or "ectodomain" of Claudin-1 refers to the region of the Claudin-1 sequence that extends into the extracellular space (i.e., the space outside a cell).

The term "antibody", as used herein, refers to any immunoglobulin (i.e., an intact immunoglobulin molecule, an active portion of an immunoglobulin molecule, etc.) that binds to a specific epitope. The term encompasses monoclonal antibodies and polyclonal antibodies. All derivatives and fragments thereof, which maintain specific binding ability, are also included in the term. The term also covers any protein having a binding domain, which is homologous or largely homologous to an immunoglobulin-binding domain. These proteins may be derived from natural sources, or partly or wholly synthetically produced.

The term "specific binding", when used in reference to an antibody, refers to an antibody binding to a predetermined antigen. Typically, the antibody binds with an affinity of at least $1 \times 10^7$ $M^{-1}$, and binds to the predetermined antigen with an affinity that is at least two-fold greater than the affinity for binding to a non-specific antigen (e.g., BSA, casein).

The term "isolated", as used herein in reference to a protein or polypeptide, means a protein or polypeptide, which by virtue of its origin or manipulation is separated from at least some of the components with which it is naturally associated or with which it is associated when initially obtained. By "isolated", it is alternatively or additionally meant that the protein or polypeptide of interest is produced or synthesized by the hand of man.

The terms "protein", "polypeptide", and "peptide" are used herein interchangeably, and refer to amino acid sequences of a variety of lengths, either in their neutral (uncharged) forms or as salts, and either unmodified or modified by glycosylation, side-chain oxidation, or phosphorylation. In certain embodiments, the amino acid sequence is a full-length native protein. In other embodiments, the amino acid sequence is a smaller fragment of the full-length protein. In still other embodiments, the amino acid sequence is modified by additional substituents attached to the amino acid side chains, such as glycosyl units, lipids, or inorganic ions such as phosphates, as well as modifications relating to chemical conversions of the chains such as oxidation of sulfhydryl groups. Thus, the term "protein" (or its equivalent terms) is intended to include the amino acid sequence of the full-length native protein, or a fragment thereof, subject to those modifications that do not significantly change its specific properties. In particular, the term "protein" encompasses protein isoforms, i.e., variants that are encoded by the same gene, but that differ in their pI or MW, or both. Such isoforms can differ in their amino acid sequence (e.g., as a result of allelic variation, alternative splicing or limited proteolysis), or in the alternative, may arise from differential post-translational modification (e.g., glycosylation, acylation, phosphorylation).

The term "analog", as used herein in reference to a protein, refers to a polypeptide that possesses a similar or identical function as the protein but need not necessarily comprise an amino acid sequence that is similar or identical to the amino acid sequence of the protein or a structure that is similar or identical to that of the protein. Preferably, in the context of the present invention, a protein analog has an amino acid sequence that is at least 30%, more preferably, at least 35%, 40%, 45%, 50%, 55%, 60%, 65%, 70%, 75%, 80%, 85%, 90%, 95% or 99% identical to the amino acid sequence of the protein.

The term "fragment" or the term "portion", as used herein in reference to a protein, refers to a polypeptide comprising an amino acid sequence of at least 5 consecutive amino acid residues (preferably, at least about: 10, 15, 20, 25, 30, 35, 40, 50, 60, 70, 80, 90, 100, 125, 150, 175, 200, 250 or more amino acid residues) of the amino acid sequence of a protein. The fragment of a protein may or may not possess a functional activity of the protein.

The term "biologically active", as used herein to characterize a protein variant, analog or fragment, refers to a molecule that shares sufficient amino acid sequence identity or homology with the protein to exhibit similar or identical properties to the protein. For, example, in many embodiments of the present invention, a biologically active fragment of an anti-Claudin 1 antibody is a fragment that retains the ability of the antibody to interfere with liver cell signalling and to reverse a patient-derived HCC risk signature.

The term "homologous" (or "homology"), as used herein, is synonymous with the term "identity" and refers to the sequence similarity between two polypeptide molecules or between two nucleic acid molecules. When a position in both compared sequences is occupied by the same base or same amino acid residue, the respective molecules are then homologous at that position. The percentage of homology between two sequences corresponds to the number of matching or homologous positions shared by the two sequences divided by the number of positions compared and multiplied by 100. Generally, a comparison is made when two sequences are aligned to give maximum homology. Homologous amino acid sequences share identical or similar amino acid sequences. Similar residues are conservative substitutions for, or "allowed point mutations" of, corresponding amino acid residues in a reference sequence. "Conservative substitutions" of a residue in a reference sequence are substitutions that are physically or functionally similar to the corresponding reference residue, e.g. that have a similar size, shape, electric charge, chemical properties, including the ability to form covalent or hydrogen bonds, or the like. Particularly preferred conservative substitutions are those fulfilling the criteria defined for an "accepted point mutation" as described by Dayhoff et al. ("Atlas of Protein Sequence and Structure", 1978, Nat. Biomed. Res. Foundation, Washington, D.C., Suppl. 3, 22: 354-352).

The terms "labeled", "labeled with a detectable agent" and "labeled with a detectable moiety" are used herein interchangeably. These terms are used to specify that an entity (e.g., an antibody) can be visualized, for example, following binding to another entity (e.g., an antigen). Preferably, a detectable agent or moiety is selected such that it generates a signal which can be measured and whose intensity is related to the amount of bound entity. Methods for labeling proteins and polypeptides, including antibodies, are well-known in the art. Labeled polypeptides can be prepared by incorporation of or conjugation to a label, that is directly or indirectly detectable by spectroscopic, photochemical, biochemical, immunochemical, electrical, optical or chemical means, or any other suitable means. Suitable detectable agents include, but are not limited to, various ligands, radionuclides, fluorescent dyes, chemiluminescent agents, microparticles, enzymes, colorimetric labels, magnetic labels, and haptens.

The terms "approximately" and "about", as used herein in reference to a number, generally include numbers that fall within a range of 10% in either direction of the number (greater than or less than the number) unless otherwise stated or otherwise evident from the context (except where such number would exceed 100% of a possible value).

Detailed Description of Certain Preferred Embodiments

As mentioned above, the present invention concerns the use of anti-claudin 1 antibodies for the prevention and/or treatment of hepatocellular carcinoma, in particular for the prevention and/or treatment of hepatocellular carcinoma that is not HCV-associated.

I—Anti-Claudin-1 Antibodies

The present Applicants have previously developed monoclonal antibodies directed against human Claudin-1 and demonstrated that these monoclonal antibodies cure HCV infection in vivo without detectable adverse effects (EP 08 305 597 and WO 2010/034812). They have now demonstrated that these monoclonal antibodies interfere with liver cell signaling and reverse a patient-derived HCC risk signature in a liver cell-based model system, and that the modulation of signaling and transcriptional reprogramming is independent of the antiviral activity of the antibody.

Human Claudin 1 (CLDN1) is a tight junction protein expressed in various tissues. In hepatocytes, it plays an important role in forming barrier separating blood and bile (Zona et al., Viruses, 2014, 6(2): 875-892). CLDN1 has been shown to play a dual role in liver disease that is HCV-associated: it is an essential host factor for HCV infection serving as a viral cell entry factor required for initiation, dissemination and maintenance of infection (Evans et al., Nature, 2007, 446(7137): 801-805; Mailly et al., "Clearance of persistent hepatitis C virus infection using a claudin-1-targeting monoclonal antibody", Nat Biotech, 2015, in iress). Moreover, CLDN1 has been reported to be involved in carcinogenesis via modulation of cell signaling (Suh et al., Oncogene, 2013, 32(41): 4873-4882) or via induction of the expression of matrix metalloproteinases (Oku et al., Cancer Res, 2006, 66(10): 5251-5257). Furthermore, CLDN1 expression has been shown to be increased in HCC compared to non-diseased liver tissue (Stebbing et al., Oncogene, 2013, 32(41): 4871-4872).

Anti-Claudin 1 antibodies that can be used in the practice of the present invention include any antibody which was raised against Claudin 1 and which can be shown to interfere with liver cell signaling and to reverse a patient-derived HCC risk signature, for example in a liver cell-based model system.

Examples of anti-Claudin 1 antibodies that can be used in the practice of the present invention include, in particular, the polyclonal and monoclonal anti-CLDN1 antibodies that were developed by the present Applicants (see EP 08 305 597 and WO 2010/034812, Fofana et al., Gastroenterology, 2010, 139(3): 953-64, 964.e1-4). As described in these documents, eight monoclonal antibodies have been produced by genetic immunization and shown to efficiently inhibit HCV infection by targeting the extracellular domain of Claudin-1. Using an infectious HCV model system and primary human hepatocytes, these monoclonal anti-CLDN1 antibodies have been demonstrated to efficiently inhibit HCV infection of all major genotypes as well as highly variable HCV quasispecies in individual patients. Furthermore, these antibodies efficiently blocked entry of highly infectious HCV escape variants that were resistant to neutralizing antibodies in six patients with HCV re-infection during liver transplantation. The monoclonal anti-Claudin 1 antibodies are called OM-4A4-D4, OM-7C8-A8, OM-6D9-A6, OM-7D4-C1, OM-6E1-B5, OM-3E5-B6, OM-8A9-A3, and OM-7D3-B3. Thus, suitable anti-Claudin 1 antibodies are monoclonal antibodies secreted by any one of the hybridoma cell lines deposited by INSERM (one of the Applicants) and GENOVAC at the DSMZ (Deutsche Sammlung von Mikro-organismen und Zellkuturen GmbH, Inhoffenstraβe 7 B, 38124 Braunschweig, Germany) on Jul. 29, 2008 under Accession Numbers DSM ACC2931, DSM ACC2932, DSM ACC2933, DSM ACC2934, DSM ACC2935, DSM ACC2936, DSM ACC2937, and DSM ACC2938 (described in EP 08 305 597 and WO 2010/034812).

Other examples of suitable anti-Claudin 1 antibodies include those disclosed in European Pat. No. EP 1 167 389, U.S. Pat. No. 6,627,439, in international patent application published under No. WO 201/132307 and in international patent applications published under No. WO 2015/014659 and No. WO 2015/014357, and in Yamashita et al., J. Pharmacol. Exp. Ther., 2015, 353(1): 112-118.

The anti-Claudin 1 antibodies suitable for use in the present invention may be polyclonal antibodies or monoclonal antibodies.

Instead of using the hybridomas described above as a source of the antibodies, the anti-Claudin 1 antibodies may be prepared by any other suitable method known in the art. For example, an anti-Claudin 1 monoclonal antibody may be prepared by recombinant DNA methods. These methods generally involve isolation of the genes encoding the desired antibody, transfer of the genes into a suitable vector, and bulk expression in a cell culture system. The genes or DNA encoding the desired monoclonal antibody may be readily isolated and sequenced using conventional procedures (e.g., using oligonucleotide probes that are capable of binding specifically to genes encoding the heavy and light chains of murine antibodies). Hybridoma cell lines may serve as a preferred source of such DNA. Suitable host cells for recombinant production of antibodies include, but are not limited to, appropriate mammalian host cells, such as CHO, HeLa, or CV1. Suitable expression plasmids include, without limitation, pcDNA3.1 Zeo, pIND(SP1), pREP8 (all commercially available from Invitrogen, Carlsbad, Calif., USA), and the like. The antibody genes may be expressed via viral or retroviral vectors, including MLV-based vectors, vaccinia virus-based vectors, and the like. Cells may be grown using standard methods, in suitable culture media such as, for example, DMEM and RPMI-1640 medium. The anti-Claudin 1 antibodies may be expressed as single chain antibodies. Isolation and purification of recombinantly produced antibodies may be performed by standard methods. For example, an anti-Claudin 1 monoclonal antibody may be recovered and purified from cell cultures by protein A purification, ammonium sulphate or ethanol precipitation, acid extraction, anion or cation exchange chromatography, phosphocellulose chromatography, hydrophobic interaction chromatography, affinity chromatography, such as Protein A column, hydroxylapatite chromatography, lectin chromatography, or any suitable combination of these methods. High performance liquid chromatography (HPLC) can also be employed for purification.

Alternatively, an anti-Claudin 1 antibody for use according to the present invention may be obtained from commercial sources.

In certain embodiments, an anti-Claudin 1 antibody is used in its native form. In other embodiments, it is truncated (e.g., via enzymatic cleavage or other suitable method) to provide immunoglobulin fragments or portions, in particular, fragments or portions that are biologically active. Biologically active fragments or portions of an anti-Claudin 1 antibody include fragments or portions that retain the ability of the antibody to interfere with liver cell signaling and reverse a patient-derived HCC risk signature, for example in a liver cell-based model system such as the 186-liver gene signature system used by the present Applicants (see Examples below), and/or the ability to prevent hepatocellular carcinoma and/or treat hepatocellular carcinoma.

A biologically active fragment or portion of an anti-Claudin 1 antibody may be a Fab fragment or portion, a F(ab')$_2$ fragment or portion, a variable domain, or one or more CDRs (complementary determining regions) of the antibody (for example an antibody that comprises all 6 CDRs of an anti-Claudin 1 monoclonal antibody. Alternatively, a biologically active fragment or portion of an anti-Claudin 1 antibody may be derived from the carboxyl portion or terminus of the antibody protein and may comprise an Fc fragment, an Fd fragment or an Fv fragment.

Anti-Claudin 1 antibody fragments of the present invention may be produced by any suitable method known in the art including, but not limited to, enzymatic cleavage (e.g., proteolytic digestion of intact antibodies) or by synthetic or recombinant techniques. F(ab')$_2$, Fab, Fv and ScFv (single chain Fv) antibody fragments can, for example, be expressed in and secreted from mammalian host cells or from $E.$ $coli$. Antibodies can also be produced in a variety of truncated forms using antibody genes in which one or more stop codons have been introduced upstream of the natural stop site. The various portions of antibodies can be joined together chemically by conventional techniques, or can be prepared as a contiguous protein using genetic engineering techniques.

Anti-Claudin 1 antibodies (or biologically active fragments thereof) suitable for use according to the present invention may be produced in a modified form, such as a fusion protein (i.e., an immunoglobulin molecule or portion linked to a polypeptide entity). Preferably, the fusion protein retains the biological property of the antibody. A polypeptide entity to be fused to an anti-Claudin 1 antibody, or a biologically active fragment thereof, may be selected to confer any of a number of advantageous properties to the resulting fusion protein. For example, the polypeptide entity may be selected to provide increased expression of the recombinant fusion protein. Alternatively or additionally, the polypeptide entity may facilitate purification of the fusion protein, for example, by acting as a ligand in affinity purification. A proteolytic cleavage site may be added to the recombinant protein so that the desired sequence can ultimately be separated from the polypeptide entity after purification. The polypeptide entity may also be selected to confer an improved stability to the fusion protein, when stability is a goal. Examples of suitable polypeptide entities include, for example, polyhistidine tags, that allow for the easy purification of the resulting fusion protein on a nickel chelating column. Glutathione-S-transferase (GST), maltose B binding protein, or protein A are other examples of suitable polypeptide entities.

An anti-Claudin 1 antibody for use according to the present invention may be re-engineered so as to optimize stability, solubility, in vivo half-life, or ability to bind additional targets. Genetic engineering approaches as well as chemical modifications to accomplish any or all of these changes in properties are well known in the art. For example, the addition, removal, and/or modification of the constant regions of an antibody are known to play a particularly important role in the bioavailability, distribution, and half-life of therapeutically administered antibodies. The antibody class and subclass, determined by the Fc or constant region of the antibody (which mediates effector functions), when present, imparts important additional properties.

Additional fusion proteins of the invention may be generated through the techniques of DNA shuffling well known in the art (see, for example, U.S. Pat. Nos. 5,605,793; 5,811,238; 5,830,721; 5,834,252; and 5,837,458).

Anti-Claudin 1 antibodies suitable for use according to the present invention may also be "humanized": sequence differences between rodent antibodies and human sequences can be minimized by replacing residues which differ from those in the human sequences by site-directed mutagenesis of individual residues or by grafting of entire regions or by chemical synthesis. Humanized antibodies can also be produced using recombinant methods. In the humanized form of the antibody, some, most or all of the amino acids outside the CDR regions are replaced with amino acids from human immunoglobulin molecules, while some, most or all amino acids within one or more CDR regions are unchanged. Small additions, deletions, insertions, substitutions or modifications of amino acids are permissible as long as they do not significantly modify the biological activity of the resulting antibody. Suitable human "replacement" immunoglobulin molecules include IgG1, IgG2, IgG2a, IgG2b, IgG3, IgG4, IgA, IgM, IgD or IgE molecules, and fragments thereof. Alternatively, the T-cell epitopes present in rodent antibodies can be modified by mutation (de-immunization) to generate non-immunogenic rodent antibodies that can be applied for therapeutic purposes in humans (see webpage: accurobio.com).

Anti-Claudin 1 antibodies (or biologically active variants or fragments thereof) suitable for use according to the present invention may be functionally linked (e.g., by chemical coupling, genetic fusion, non-covalent association or otherwise) to one or more other molecular entities. Methods for the preparation of such modified antibodies (or conjugated antibodies) are known in the art (see, for example, "*Affinity Techniques. Enzyme Purification: Part B*", Methods in Enzymol., 1974, Vol. 34, Jakoby and Wilneck (Eds.), Academic Press: New York, N.Y.; and Wilchek and Bayer, Anal. Biochem., 1988, 171: 1-32). Preferably, molecular entities are attached at positions on the antibody molecule that do not interfere with the binding properties of the resulting conjugate, e.g., positions that do not participate in the specific binding of the antibody to its target.

The antibody molecule and molecular entity may be covalently, directly linked to each other. Or, alternatively, the antibody molecule and molecular entity may be covalently linked to each other through a linker group. This can be accomplished by using any of a wide variety of stable bifunctional agents well known in the art, including homofunctional and heterofunctional linkers.

In certain embodiments, an anti-Claudin 1 antibody (or a biologically active fragment thereof) for use according to the present invention is conjugated to a therapeutic moiety. Any of a wide variety of therapeutic moieties may be suitable for use in the practice of the present invention including, without limitation, cytotoxins (e.g., cytostatic or cytocidal agents), therapeutic agents, and radioactive metal ions (e.g., alpha-emitters and alpha-emitters attached to macrocyclic chelators such as DOTA). Cytotoxins or cytotoxc agents include any agent that is detrimental to cells. Examples include, but are not limited to, paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, thymidine kinase, endonuclease, RNAse, and puromycin and fragments, variants or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin and doxorubicin), antibiotics (e.g., dactinomycin, bleomycin, mithramycin, and anthramycin), and anti-mitotic agents (e.g., vincristine and vinblastine).

Other therapeutic moieties include proteins or polypeptides possessing a desired biological activity. Such proteins include, but are not limited to, toxins (e.g., abrin, ricin A, alpha toxin, *pseudomonas* exotoxin, diphtheria toxin, saporin, momordin, gelonin, pokeweed antiviral protein, alpha-sarcin and cholera toxin); proteins such as tumor necrosis factor, alpha-interferon, beta-interferon, nerve growth factor, platelet derived growth factor, tissue plasminogen activator; apoptotic agents (e.g., TNF-$\alpha$, TNF-$\beta$) or, biological response modifiers (e.g., lymphokines, interleukin-1 (IL-1), interleukin-2 (IL-2), interleukin-6 (IL-6), granulocyte macrophage colony stimulating factor (GM-CSF), granulocyte colony stimulating factor (G-CSF), or other growth factors).

Alternatively or additionally, an antibody of the present invention (or a biologically active fragment thereof) may be conjugated to a detectable agent. Any of a wide variety of detectable agents can be used in the practice of the present invention, including, without limitation, various ligands, radionuclides (e.g. $^3$H, $^{125}$I, $^{131}$I, and the like), fluorescent dyes (e.g., fluorescein isothiocyanate, rhodamine, phycoerytherin, phycocyanin, allophycocyanin, o-phthalaldehyde and fluorescamine), chemiluminescent agents (e.g., luciferin, luciferase and aequorin), microparticles (such as, for example, quantum dots, nanocrystals, phosphors and the like), enzymes (such as, for example, those used in an ELISA, i.e., horseradish peroxidase, beta-galactosidase, luciferase, alkaline phosphatase), colorimetric labels, magnetic labels, and biotin, dioxigenin or other haptens and proteins for which antisera or monoclonal antibodies are available.

Other molecular entities that can be conjugated to an antibody of the present invention (or a biologically active fragment thereof) include, but are not limited to, linear or branched hydrophilic polymeric groups, fatty acid groups, or fatty ester groups.

Thus, in the practice of the present invention, anti-Claudin 1 antibodies can be used under the form of full length antibodies, biologically active variants or fragments thereof, chimeric antibodies, humanized antibodies, and antibody-derived molecules comprising at least one complementary determining region (CDR) from either a heavy chain or light chain variable region of an anti-Claudin 1 antibody, including molecules such as Fab fragments, F(ab')$_2$ fragments, Fd fragments, Fabc fragments, Sc antibodies (single chain antibodies), diabodies, individual antibody light single chains, individual antibody heavy chains, chimeric fusions between antibody chains and other molecules, and antibody conjugates, such as antibodies conjugated to a therapeutic agent or a detectable agent. Preferably, anti-Claudin 1 antibody-related molecules according to the present invention will be shown to interfere with liver cell signaling and to reverse a patient-derived HCC risk signature (such as the 186-liver gene signature system used by the present Applicants—see Examples).

One skilled in the art will understand that other compounds targeting Claudin-1, can be used in the practice of the present invention, including, but not limited to, small molecules and siRNAs.

II—Treatment or Prevention of Hepatocellular Carcinoma
A. Indications

The present Applicants have shown that anti-Claudin 1 antibodies are more potent than antiviral agents and other candidate compounds for HCC chemoprotection at reversing HCC high-risk signature. Therefore, anti-Claudin 1 antibodies, or biologically active fragments thereof, may be used in prophylactic and therapeutic methods to prevent and/or treat hepatocellular carcinoma.

Methods of treatment of the present invention may be accomplished using an anti-Claudin 1 antibody, or a biologically active fragment thereof, or a pharmaceutical composition comprising such an antibody or fragment (see below). These methods generally comprise administration of an effective amount of an anti-Claudin-1 antibody, or biologically active fragment thereof, or of a pharmaceutical composition thereof, to a subject in need thereof. Administration may be performed using any of the administration methods known to one skilled in the art (see below).

In particular, the present invention provides a method for preventing a patient suffering from a liver disease from developing hepatocellular carcinoma. The liver disease or pathology may be inflammation of the liver, liver fibrosis, and/or cirrhosis.

In the practice of the present invention, the underlying cause of the liver disease is not HCV infection. Thus, the invention provides a method for preventing and/or treating non-HCV-associated hepatocellular carcinoma, i.e., for preventing and/or treating hepatocellular carcinoma that develops, or that is susceptible of developing, in a patient who has never been infected with HCV, or in a patient who has been cured from HCV infection.

In certain embodiments of the invention, the underlying cause of the liver disease is HBV infection. Chronic infection with HBV leads to cirrhosis of the liver and is, with chronic HCV infection, responsible for making liver cancer the most common cancer in many parts of the world. Worldwide, around 2 billion people are infected with HBV. HCC risk is around 20 times higher in people with HBV and/or HCV infection in Western industrialized countries, where prevalence of infection is low.

Alternatively, the liver disease may be alcoholic liver disease, where the underlying cause of the liver disease is alcoholism. Alcohol intake has been definitely recognized as a cause of chronic liver diseases, including hepatocellular carcinoma. Alcohol could be involved in the development of HCC through both direct (genotoxic) and indirect mechanisms. An indirect mechanism includes the development of cirrhosis, which is probably the most common pathway to liver carcinogenesis in developed countries.

In other embodiments of the preset invention, the underlying cause of the liver disease is non-alcoholic fatty liver disease (NAFLD). NAFLD is the most common liver disorder in the Western industrialized countries. It is considered to be the hepatic manifestation of the metabolic syndrome. Thus, NAFLD tends to develop in people who are overweight or obese, and/or who have diabetes, high cholesterol or high triglycerides. For most people, NAFLD cause no signs and symptoms, and no complications. But in some people with NAFLD, the fat that accumulates in the liver can cause inflammation and scarring in the liver that is believed to result in fibrosis and cirrhosis. This more serious form of NAFLD is sometimes called non-alcoholic steatohepatitis. It is worth noting that metabolic syndrome and type 2 diabetes have been demonstrated to be independent risk factors of HCC.

In yet other embodiments, the underlying cause of the liver disease is an inherited metabolic disease, such as hereditary hemochromatosis. People with hereditary hemochromatosis absorb too much iron from their food. The iron settles in tissues throughout the body, including the liver. If enough iron builds up in the liver, it can lead to cirrhosis. Other inherited metabolic diseases that are risk factors for hepatocellular carcinoma include, alpha 1 antitrypsin deficiency, *porphyria* cutanea *tarda*, Wilson's disease, tyrosinemia, and glycogen storage diseases.

In still other embodiments, the underlying cause of the liver disease is autoimmune hepatitis (also called lupoid hepatitis). Autoimmune hepatitis is a chronic disease of the liver that occurs when the body's immune system attacks cells of the liver causing the liver to be inflamed. Another autoimmune disease that affects the liver and can cause cirrhosis is primary biliary cirrhosis or PBC. PBC is an autoimmune condition, in which the immune system slowly attacks the bile ducts in the liver. When the bile ducts are damaged, bile builds up in the liver and over time damages the tissue. This can lead to scaring, fibrosis and cirrhosis.

In other embodiments, the underlying cause of liver disease is exposure to aflatoxins. Aflatoxins are poisons produced by a fungus that grows on crops (such as peanuts, wheat, soybeans, corn, and rice) that are stored poorly. Long term exposure to these substances is a major risk for liver cancer. The risk is increased even more in people with HCV or HBV infection. In developed countries, the content of aflatoxin in foods is regulated through testing. Aflatoxin contamination is more common in certain parts of Africa and Asia.

In still other embodiments, the underlying cause of liver disease is unknown or the liver disease is caused by yet to be discovered agents including agents of genetic origin, infectious agents or chemical and/or physical liver toxic agents.

Administration of an anti-Claudin 1 antibody, or of a pharmaceutical composition thereof, to patients suffering from non-HCV associated liver diseases according to the present invention may slow, reduce, stop or alleviate the progression of the liver disease, in particular the progression to cirrhosis and/or to hepatocellular carcinoma, or reverse the progression to the point of curing the liver disease.

Alternatively or additionally, administration of an anti-Claudin 1 antibody, or of a pharmaceutical composition thereof, to a patient suffering from a non-HCV associated liver disease according to the present invention may result in amelioration of at least one of the symptoms experienced by the individual including, but not limited to, decreased appetite, weight loss, fatigue, abdominal pain, jaundice, itching, flu-like symptoms, muscle pain, joint pain, intermittent low-grade fevers, itching, sleep disturbances, nausea, diarrhea, dyspepsia, cognitive changes, depression, headaches, and mood swings; symptoms of cirrhosis such as ascites, bruising and bleeding tendency, bone pain, varices (especially in the stomach and esophagus), steatorrhea, jaundice and hepatic encephalopathy.

Alternatively or additionally, administration of an anti-Claudin 1 antibody, or o a pharmaceutical composition thereof, to a patient suffering from a non-HCV associated liver disease according to the present invention may result in prevention of liver transplantation.

The effects of a treatment according to the invention may be monitored using any of the assays known in the art for the diagnosis of the liver disease affecting the patient. Such assays include, but are not limited to, serological blood tests, and liver function tests to measure one or more of albumin, alanine transaminase (ALT), alkaline phosphatase (ALP), aspartate transaminase (AST), and gamma glutamyl transpeptidase (GGT), and liver imaging techniques such as magnetic resonance elastography (MRE), magnetic resonance imaging (MRI), computerized tomography (CT) and ultrasound. Biopsy may also be performed.

Such assays may also include analysis of liver cell signaling, transcriptional or proteomic changes, as described in the Examples below, in a biological sample obtained from the subject receiving a treatment according to the present invention. Liver cells that can be analyzed include hepatocytes, Kupffer cells, stellate cells, endothelial cells, fibroblasts, macrophages, and immune cells including, but not limited to, T-, B- and NK cells.

In certain embodiments, an anti-Claudin 1 antibody (or a biologically active fragment thereof) or a pharmaceutical composition thereof, is administered alone according to a method of prevention or treatment of the present invention. In other embodiments, an anti-Claudin 1 antibody (or a biologically active fragment thereof) or a pharmaceutical composition thereof, is administered in combination with at least one additional therapeutic agent. The anti-Claudin 1 antibody (or biologically active fragment thereof), or pharmaceutical composition thereof, may be administered prior to administration of the therapeutic agent, concurrently with the therapeutic agent, and/or following administration of the therapeutic agent.

Therapeutic agents that may be administered in combination with an anti-Claudin 1 antibody (or biologically active fragment thereof), or a pharmaceutical composition thereof, may be selected among a large variety of biologically active compounds that are known in the art to have a beneficial effect in the treatment of liver disease and/or in the treatment of the underlying cause of the liver disease. As will be understood by one skilled in the art, the therapeutic agent(s) will differ depending on the nature of the liver disease that affects the patient.

For example, when the patient is suffering from a liver disease associated with HBV infection, the therapeutic agent(s) may be pegylated interferon (PEG-IFN) or nucleoside or nucleotide analogues that are used in the prevention of HCC in HBV infected patients. In the case of alcoholic liver disease, the therapeutic agent(s) may be corticosteroids and/or antioxidants such as S-adenosyl methionine. When the patient has non-alcoholic fatty liver disease, the therapeutic agent(s) may be insulin sensitizers (such as metformin and thiazolidinediones, e.g. Pioglitazone), ursodeoxycholic acid and lipid-lowering drugs, vitamin E, and statins. In the case of hereditary hemochromatosis, the therapeutic agent(s) may be iron chelation drugs (such as chloroquine and hydroxychloroquine). For alpha 1 antitrypsin deficiency liver disease, the therapeutic agent(s) may be inhaled forms of alpha 1 antitrypsin. For *porphyria* cutanea *tarda*, the therapeutic agent(s) may be iron chelating drugs (such as chloroquine and hydroxychloroquine). In the case of Wilson's disease, the therapeutic agent(s) may be cupper chelating drugs (such as penicillamine and trientine hydrochloride) and zinc acetate, which prevent the body from absorbing copper from food. In the case of autoimmune hepatitis, the therapeutic agent(s) may be corticosteroids and/or immune system suppressors. For primary biliary cirrhosis, the therapeutic agent(s) may be ursodeoxycholic acid (which is the major medication to show the progression of the disease), immunosuppressive agents, methothrexate, corticosteroids, cyclosporine and antipruritic agents.

B. Administration

An anti-Claudin 1 antibody, or a biologically active fragment thereof, (optionally after formulation with one or more appropriate pharmaceutically acceptable carriers or excipients), in a desired dosage, can be administered to a subject in need thereof by any suitable route. Various delivery systems are known and can be used to administer antibodies, including tablets, capsules, injectable solutions, encapsulation in liposomes, microparticles, microcapsules, etc. Methods of administration include, but are not limited to, dermal, intradermal, intramuscular, intraperitoneal, intralesional, intravenous, subcutaneous, intranasal, pulmonary, epidural, ocular, and oral routes. An anti-Claudin 1 antibody, or a biologically active fragment thereof, or a pharmaceutical composition thereof, may be administered by any convenient or other appropriate route, for example, by infusion or bolus injection, by absorption through epithelial or mucocutaneous linings (e.g., oral, mucosa, rectal and intestinal mucosa, etc). Administration can be systemic or local. Parenteral administration may be preferentially directed to the patient's liver, such as by catheterization to hepatic arteries or into a bile duct or into the portal vein. As will be appreciated by those of ordinary skill in the art, in embodiments where an inventive antibody is administered in combination with an additional therapeutic agent, the antibody and therapeutic agent may be administered by the same route (e.g., intravenously) or by different routes (e.g., intravenously and orally).

C. Dosage

An anti-Claudin 1 antibody, or a biologically active fragment thereof, (optionally after formulation with one or more appropriate pharmaceutically acceptable carriers or excipients), will be administered in a dosage such that the amount delivered is effective for the intended purpose. The route of administration, formulation and dosage administered will depend upon the therapeutic effect desired, the severity of the condition to be treated if already present, the presence of any infection, the age, sex, weight, and general health condition of the patient as well as upon the potency, bioavailability, and in vivo half-life of the antibody or composition used, the use (or not) of concomitant therapies, and other clinical factors. These factors are readily determinable by the attending physician in the course of the therapy. Alternatively or additionally, the dosage to be administered can be determined from studies using animal models (e.g., chimpanzee or mice). Adjusting the dose to achieve maximal efficacy based on these or other methods are well known in the art and are within the capabilities of trained physicians. As studies are conducted using anti-Claudin 1 antibodies, further information will emerge regarding the appropriate dosage levels and duration of treatment.

A treatment according to the present invention may consist of a single dose or multiple doses. Thus, administration of an anti-Claudin 1 antibody, or a biologically active fragment thereof, (or a pharmaceutical composition thereof) may be constant for a certain period of time or periodic and at specific intervals, e.g., hourly, daily, weekly (or at some other multiple day interval), monthly, yearly (e.g., in a time release form). Alternatively, the delivery may occur at multiple times during a given time period, e.g., two or more times per week; two or more times per month, and the like. The delivery may be continuous delivery for a period of time, e.g., intravenous delivery.

In general, the amount of anti-Claudin 1 antibody, or a biologically active fragment thereof, (or a pharmaceutical composition thereof) administered will preferably be in the range of about 1 ng/kg to about 100 mg/kg body weight of the subject, for example, between about 100 ng/kg and about 50 mg/kg body weight of the subject; or between about 1 µg/kg and about 10 mg/kg body weight of the subject, or between about 100 µg/kg and about 1 mg/kg body weight of the subject.

In certain embodiments, the amount of anti-Claudin 1 antibody, or of a biologically active fragment thereof, (or of a pharmaceutical composition thereof) administered will be such that the amount would have no effect on HCV load if it had been administered to a HCV infected patient.

III—Pharmaceutical Compositions

As mentioned above, anti-Claudin-1 antibodies (and related molecules) may be administered per se or as a pharmaceutical composition. Accordingly, the present invention provides pharmaceutical compositions comprising an effective amount of an anti-Claudin 1 antibody, or a biologically active fragment thereof, described herein and at least one pharmaceutically acceptable carrier or excipient for use in the prevention or treatment of hepatocellular carcinoma. In some embodiments, the composition further comprises one or more additional biologically active agents.

The antibodies or pharmaceutical compositions may be administered in any amount and using any route of administration effective for achieving the desired prophylactic and/or therapeutic effect. The optimal pharmaceutical formulation can be varied depending upon the route of administration and desired dosage. Such formulations may influence the physical state, stability, rate of in vivo release, and rate of in vivo clearance of the administered active ingredient.

The pharmaceutical compositions of the present invention may be formulated in dosage unit form for ease of administration and uniformity of dosage. The expression "unit dosage form", as used herein, refers to a physically discrete unit of an anti-Claudin-1 antibody, or a biologically active fragment thereof, for the patient to be treated. It will be understood, however, that the total daily dosage of the compositions will be decided by the attending physician within the scope of sound medical judgement.

A. Formulation

Injectable preparations, for example, sterile injectable aqueous or oleaginous suspensions may be formulated according to the known art using suitable dispersing or wetting agents, and suspending agents. The sterile injectable preparation may also be a sterile injectable solution, suspension or emulsion in a non-toxic parenterally acceptable diluent or solvent, for example, as a solution in 2,3-butanediol. Among the acceptable vehicles and solvents that may be employed are water, Ringer's solution, U.S.P. and isotonic sodium chloride solution. In addition, sterile, fixed oils are conventionally employed as a solution or suspending medium. For this purpose, any bland fixed oil can be employed including synthetic mono- or di-glycerides. Fatty acids such as oleic acid may also be used in the preparation of injectable formulations. Sterile liquid carriers are useful in sterile liquid form compositions for parenteral administration.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. Liquid pharmaceutical compositions which are sterile solutions or suspensions can be administered by, for example, intravenous, intramuscular, intraperitoneal or subcutaneous injection. Injection may be via single push or by gradual infusion. Where necessary or desired, the composition may include a local anesthetic to ease pain at the site of injection.

In order to prolong the effect of an active ingredient (here an anti-Claudin-1 antibody, or a biologically active fragment thereof), it is often desirable to slow the absorption of the ingredient from subcutaneous or intramuscular injection. Delaying absorption of a parenterally administered active ingredient may be accomplished by dissolving or suspending the ingredient in an oil vehicle. Injectable depot forms are made by forming micro-encapsulated matrices of the active ingredient in biodegradable polymers such as polylactide-polyglycolide. Depending upon the ratio of active ingredient to polymer and the nature of the particular polymer employed, the rate of ingredient release can be controlled. Examples of other biodegradable polymers include poly(orthoesters) and poly(anhydrides). Depot injectable formulations can also be prepared by entrapping the active ingredient in liposomes or microemulsions which are compatible with body tissues.

Liquid dosage forms for oral administration include, but are not limited to, pharmaceutically acceptable emulsions, microemulsions, solutions, suspensions, syrups, elixirs, and pressurized compositions. In addition to the anti-Claudin-1 antibody, or biologically active fragment thereof, the liquid dosage form may contain inert diluents commonly used in the art such as, for example, water or other solvent, solubilising agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cotton seed, ground nut, corn, germ, olive, castor, and sesame oils), glycerol, tetrahydrofurfuryl alcohol, polyethylene glycols, and fatty acid esters of sorbitan and mixtures thereof. Besides inert diluents, the oral compositions can also include adjuvants such as wetting agents, suspending agents, preservatives, sweetening, flavouring, and perfuming agents, thickening agents, colors, viscosity regulators, stabilizes or osmo-regulators. Examples of suitable liquid carriers for oral administration include water (potentially containing additives as above, e.g., cellulose derivatives, such as sodium carboxymethyl cellulose solution), alcohols (including monohydric alcohols and polyhydric alcohols such as glycols) and their derivatives, and oils (e.g., fractionated coconut oil and *arachis* oil). For pressurized compositions, the liquid carrier can be halogenated hydrocarbon or other pharmaceutically acceptable propellant.

Solid dosage forms for oral administration include, for example, capsules, tablets, pills, powders, and granules. In such solid dosage forms, an anti-Claudin-1 antibody, or a biologically active fragment thereof may be mixed with at least one inert, physiologically acceptable excipient or carrier such as sodium citrate or dicalcium phosphate and one or more of: (a) fillers or extenders such as starches, lactose, sucrose, glucose, mannital, and silicic acid; (b) binders such as, for example, carboxymethylcellulose, alginates, gelatine, polyvinylpyrrolidone, sucrose, and acacia; (c) humectants such as glycerol; (d) disintegrating agents such as agar-agar, calcium carbonate, potato or tapioca starch, alginic acid, certain silicates, and sodium carbonate; (e) solution retarding agents such as paraffin; absorption accelerators such as quaternary ammonium compounds; (g) wetting agents such as, for example, cetyl alcohol and glycerol monostearate; (h) absorbents such as kaolin and bentonite clay; and (i) lubricants such as talc, calcium stearate, magnesium stearate, solid polyethylene glycols, sodium lauryl sulphate, and mixtures thereof. Other excipients suitable for solid formulations include surface modifying agents such as non-ionic and anionic surface modifying agents. Representative examples of surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine. In the case of capsules, tablets and pills, the dosage form may also comprise buffering agents.

Solid compositions of a similar type may also be employed as fillers in soft and hard-filled gelatine capsules using such excipients as lactose or milk sugar as well as high molecular weight polyethylene glycols and the like. The solid dosage forms of tablets, dragees, capsules, pills, and granules can be prepared with coatings and shells such as enteric coatings, release controlling coatings and other coatings well known in the pharmaceutical formulating art. They may optionally contain opacifying agents and can also be of a composition such that they release the active ingredient(s) only, or preferably, in a certain part of the intestinal tract, optionally, in a delaying manner. Examples of embedding compositions which can be used include polymeric substances and waxes.

In certain embodiments, it may be desirable to administer an inventive composition locally to an area in need of treatment (e.g., the liver). This may be achieved, for example, and not by way of limitation, by local infusion during surgery (e.g., liver transplant), topical application, by injection, by means of a catheter, by means of suppository, or by means of a skin patch or stent or other implant.

For topical administration, the composition is preferably formulated as a gel, an ointment, a lotion, or a cream which can include carriers such as water, glycerol, alcohol, propylene glycol, fatty alcohols, triglycerides, fatty acid esters, or mineral oil. Other topical carriers include liquid petroleum, isopropyl palmitate, polyethylene glycol, ethanol (95%), polyoxyethylenemonolaurat (5%) in water, or sodium lauryl sulphate (5%) in water. Other materials such as antioxidants, humectants, viscosity stabilizers, and similar agents may be added as necessary.

In addition, in certain instances, it is expected that the pharmaceutical compositions may be disposed within transdermal devices placed upon, in, or under the skin. Such devices include patches, implants, and injections which release the active ingredient by either passive or active release mechanisms. Transdermal administrations include all administration across the surface of the body and the inner linings of bodily passage including epithelial and mucosal tissues. Such administrations may be carried out using the present compositions in lotions, creams, foams, patches, suspensions, solutions, and suppositories (rectal and vaginal).

Transdermal administration may be accomplished through the use of a transdermal patch containing an active ingredient (i.e., an anti-Claudin-1 antibody, or a biologically active fragment thereof) and a carrier that is non-toxic to the skin, and allows the delivery of the ingredient for systemic absorption into the bloodstream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may be suitable. A variety of occlusive devices may be used to release the active ingredient into the bloodstream such as a semi-permeable membrane covering a reservoir containing the active ingredient with or without a carrier, or a matrix containing the active ingredient.

Suppository formulations may be made from traditional materials, including cocoa butter, with or without the addition of waxes to alter the suppository's melting point, and glycerine. Water soluble suppository bases, such as polyethylene glycols of various molecular weights, may also be used.

Materials and methods for producing various formulations are known in the art and may be adapted for practicing the subject invention. Suitable formulations for the delivery of antibodies can be found, for example, in "Remington's Pharmaceutical Sciences", E.W. Martin, 18$^{th}$ Ed., 1990, Mack Publishing Co.: Easton, Pa.

B. Additional Biologically Active Agents

In certain embodiments, an anti-Claudin-1 antibody, or a biologically active fragment thereof, is the only active ingredient in a pharmaceutical composition of the present invention. In other embodiments, the pharmaceutical composition further comprises one or more biologically active agents. Examples of suitable biologically active agents include, but are not limited to, therapeutic agents such as anti-viral agents, anti-inflammatory agents, immunomodulatory agents, analgesics, antimicrobial agents, kinase inhibitors, signalling inhibitors, antibacterial agents, antibiotics, antioxidants, antiseptic agents, and combinations thereof.

In such pharmaceutical compositions, the anti-Claudin-1 antibody and additional therapeutic agent(s) may be combined in one or more preparations for simultaneous, separate or sequential administration of the anti-Claudin-1 antibody and therapeutic agent(s). More specifically, an inventive composition may be formulated in such a way that the antibody and therapeutic agent(s) can be administered together or independently from each other. For example, an anti-Claudin-1 antibody and a therapeutic agent can be formulated together in a single composition. Alternatively, they may be maintained (e.g., in different compositions and/or containers) and administered separately.

C. Pharmaceutical Packs of Kits

In another aspect, the present invention provides a pharmaceutical pack or kit comprising one or more containers (e.g., vials, ampoules, test tubes, flasks or bottles) containing one or more ingredients of an inventive pharmaceutical composition, allowing administration of an anti-Claudin-1 antibody, or a biologically active fragment thereof.

Different ingredients of a pharmaceutical pack or kit may be supplied in a solid (e.g., lyophilized) or liquid form. Each ingredient will generally be suitable as aliquoted in its respective container or provided in a concentrated form. Pharmaceutical packs or kits may include media for the reconstitution of lyophilized ingredients. Individual containers of the kits will preferably be maintained in close confinement for commercial sale.

In certain embodiments, a pharmaceutical pack or kit includes one or more additional therapeutic agent(s) as described above. Optionally associated with the container(s) can be a notice or package insert in the form prescribed by a governmental agency regulating the manufacture, use or sale of pharmaceutical or biological products, which notice reflects approval by the agency of manufacture, use or sale for human administration. The notice of package insert may contain instructions for use of a pharmaceutical composition according to methods of treatment disclosed herein.

An identifier, e.g., a bar code, radio frequency, ID tags, etc., may be present in or on the kit. The identifier can be used, for example, to uniquely identify the kit for purposes of quality control, inventory control, tracking movement between workstations, etc.

EXAMPLES

The following examples describe some of the preferred modes of making and practicing the present invention. However, it should be understood that the examples are for illustrative purposes only and are not meant to limit the scope of the invention. Furthermore, unless the description in an Example is presented in the past tense, the text, like the rest of the specification, is not intended to suggest that experiments were actually performed or data are actually obtained.

Some of the results reported below are presented in a manuscript: T. Baumert et al., "A Claudin-1-specific Monoclonal Antibody for Prevention and Treatment of Hepatocellular Carcinoma", which has been submitted for publication.

Example 1

Materials and Methods

Reagents and Antibodies.

The anti-claudin-1 monoclonal antibodies (anti-CLDN1 mAbs were produced as previously described (Fofana et al., Gastroenterology, 2010, 139: 953-964, e1-4). Erlotinib was purchased from IC Laboratories; and interferon-alpha 2a from Roche. Daclatasvir and sofosbuvir were synthesized by Acme Biosciences. Pioglitazone, metformin and DMSO were purchased from Sigma-Aldrich. The Human Phospho-RTK Array kit was obtained from R&D Systems. The ECL reagent and Hyperfilms were purchased from GE Healthcare. The Alexa-Fluor® 647 anti-mouse IgG (goat) and Alexa-Fluor® 647 anti-human IgG (goat) were purchased from Jackson ImmunoResearch. Dapi was obtained from Life Technologies.

Cell Lines.

Huh7.5.1 cells have already been described (Zhong et al., Proc Natl Acad Sci USA, 2005, 102(26): 9294-9299). For proliferation arrest and differentiation (Huh7.5.1$^{dif}$ cells), $2.5 \cdot 10^4$ to $3 \cdot 10^4$ Huh7.5.1 cells were cultured in Dulbecco's Modified Eagle Medium (DMEM) containing 1% dimethylsulfoxide (DMSO).

HCV Infection of Huh7.5.1$^{dif}$ Cells.

Cell culture-derived HCVcc Jc1 (genotype 2a/2a) (Pietschmann et al., Proc Natl Acad Sci USA, 2006, 103(19): 7408-7413) were generated in Huh7.5.1 cells as previously described (Wakita et al., Nat Med., 2005, 11(7): 791-796). HCVcc infectivity was determined by calculating the 50% tissue culture infectious doses (TCID$_{50}$) in infection experiments as previously described (Lindenbach et al., Science, 2005, 309(5734): 623-626). HCV infection was assessed by qRT-PCR of intracellular HCV RNA (Xiao et al., Gut, 2015, 64(3): 483-494) as well as by immunostaining using an HCV E2-specific AP33 antibody as previously described (Krieger et al., Hepatology. 2010, 51(4): 1144-1157).

Transcriptional Analyses.

Liver cells were lysed in TRI-reagent (Molecular Research Center), and RNA was purified using Direct-zol RNA MiniPrep (Zymo Research) according to the manufacturer's instructions. RNA quantity and quality were assessed using NanoDrop (ThermoScientific) and Bioanalyzer 2100 (Illumina). Gene expression profiling was performed using 250-500 ng total RNA by using nCounter Digital Analyzer system (NanoString).

Analysis of Phosphorylation.

Phospho-array analysis was performed using the Proteome Prolifer Human Phospho-kinase Array (R&D Systems) as previously described by the manufacturer. For imaging, blots were incubated with ECL (GE Healthcare) and exposed to ECL Hyperfilm (GE Heathcare). Phospho-kinase array results were quantified by integrating the dot blot densities using Image J software (NIH).

Effect of Antivirals and Small Molecules on HCC Risk Signature.

Seven (7) days after HCV Jc1 infection, Huh7.5.1$^{dif}$ cells were incubated with either a combination of 1 nM daclatasvir and 1 µM sofosbuvir; 10 IU/mL interferon-alpha 2a; 1, 10 or 100 µg/mL CLDN1-specific mAb; or 0.1 mM erlotinib in the presence of 1% DMSO. Cells incubated with 1% DMSO served as negative control. Three (3) days after treatment, the cells were lysed, total RNA was purified as described above, and analyzed for gene expression and intracellular viral load as described above.

Bioinformatic and Statistical Analyses.

Prediction of clinical outcome based on the 186-gene signature was performed as previously reported by using the nearest template prediction algorithm, which was implemented in GenePattern (King et al., Gut, 2014, 20. pii: gutjnl-2014-307862. doi: 10.1136/gutjnl-2014-307862; Hoshida et al., PLoS ONE, 2010, 5(11), e15543). A prediction of HCC high-risk or low-risk gene signature was determined using p<0.05 and FDR<0.25. Induction/suppression of each gene set over time according to HCV Jc1 infection and uninfected control was assessed through GSEA and single sample GSEA (ssGSEA) modules implemented in GenePattern as previously described (Subramanian et al., Proc Natl Acad Sci USA, 2005, 102(43): 15545-15550; Barbie et al., Nature, 2009, 462(7269): 108-112). Pathway enrichment analysis was performed using ToppGene Suite (webpage: toppgene.cchmc.org) as previously described (Chen et al., Nucleic Acids Res., 2009, 37 (Web Server issue): W305-311). nCounter assay genes were considered significantly expressed with t-test FDR<0.05 and fold changes of ±1.8. Using differentially expressed genes, network analysis was performed using canonical pathways from Ingenuity Knowledge Base repository (Ingenuity Systems Inc.).

Results

186-Gene HCC Risk Signature.

The present study makes use of a 186-gene HCC risk signature in non-cancerous liver tissue, which has been shown to be strongly associated with HCC predictive risk in patients with cirrhosis caused by hepatitis C virus (HCV), hepatitis B virus (HBV) and alcoholism (Hoshida et al., N Engl J Med., 2008, 359(19): 1995-2004; Hoshida et al., Gastroenterology. 2013, 144(5): 1024-1030; King et al., Gut, 2014, 20. pii: gutjnl-2014-307862. doi: 10.1136/gutjnl-2014-307862; King et al., PLoS ONE, 2014, 9(12): e114747) in multiple independent cohorts of Asian, European, and American patients with cirrhosis and HCC caused by multiple etiologies based on up to 23 years of follow-up. This gene signature comprised 73 HCC high-risk genes in liver, which were up-regulated, and 103 HCC low-risk genes, which were down-regulated in liver tissues (Hoshida et al., Gastroenterology. 2013, 144(5): 1024-1030).

Molecular pathway analysis had revealed that chronic HCV infection in the human liver enhances activation of NF-κB, interleukin-6, as well as epidermal growth factor (EGF) pathways and suppresses DNA repair-related genes (Hernandez-Gea et al., Gastroenterology, 2013, 144(3): 512-527). The signature demonstrated substantially superior prognostic capability (Hoshida et al., J Hepatol., 2014, 61(1S): S79-S90) compared to prognostic DNA variants identified in large-scale case-control or cohort studies (Kumar et al., Nat Genet., 2011, 43(5): 455-458; Miki et al., Nat Genet., 2011, 43(8): 797-800; Abu Dayyeh et al., Gastroenterology, 2011, 141(1): 141-149). In rodent models of cirrhosis-driven HCC, the signature was induced from a very early stage of liver fibrosis, and reversed in response to the FDA-approved EGF pathway inhibitor erlotinib, accompanied with reduced liver fibrosis and HCC nodules (Fuchs et al., Hepatology, 2014, 59(4): 1577-1590).

Thus, the 186-gene HCC risk signature represents a valuable tool to monitor progression of HCC and to understand what pathways play a role in HCC development. Taking advantage of this observation, the present Applicants have recently developed a simple and robust liver cell-based system with inducible 186-gene HCC risk signature. The HCC high-risk signature was induced by persistent HBV infection, HCV infection or ethanol exposure. Using this model, they have identified drivers of the HCC high-risk signature, including EGFR signaling, and showed reversal of the HCC high-risk signature by erlotinib (S. Bandiera et al., "A cell-based model unravels drivers for hepatocarcinogenesis and targets for clinical chemoprevention", which was submitted for publication to Nature Medicine on Mar. 12, 2015. This cell-based model enables to unravel the cell circuits of liver disease progression in patients and to identify HCC chemoprevention targets for clinical evaluation.

A CLDN1-specific mAb was found to reverse the HCC high-risk gene expression signature in a liver cell-based model for liver disease progression and hepatocarcinogenesis.

Figure 1B:
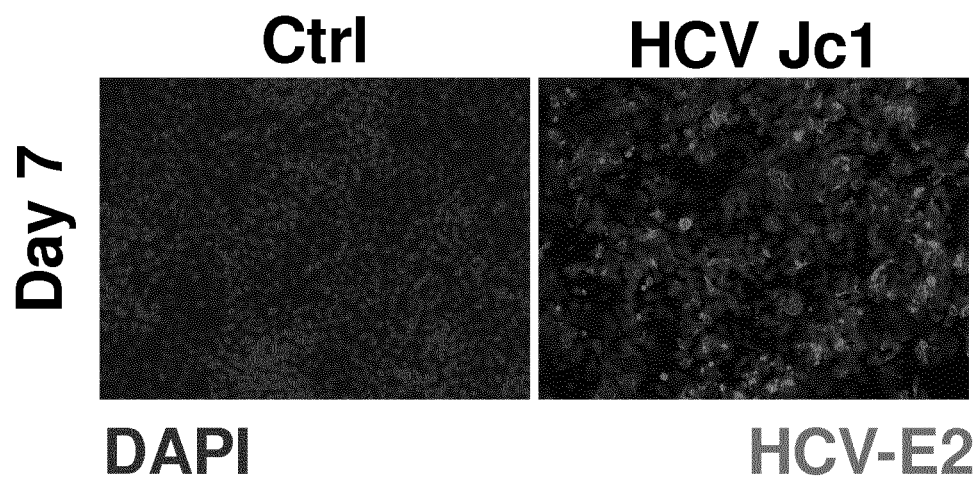

To evaluate the role of the anti-CLDN1 mAb for HCC chemoprevention, the Applicants used a previously developed model based on poorly proliferative Huh7.5.1 cells (Huh7.5.1$^{dif}$) in which the HCC-related 186-gene signature can be readily induced upon exposure to recombinant HCV (strain Jc1—Bauhofer et al., Gastroenterology, 2012, 143 (2): 429-438 e8) (see FIG. 1A). The CLDN1-specific mAb was added to Huh7.5.1$^{dif}$ cells 7 days after viral inoculation, a time point at which the vast majority of cells was persistently infected with HCV as assessed by immunocytochemical assay (see FIG. 1B). Ertolinib was used as a positive control for reversal of the gene signature. The effect of the CLDN1-specific mAb treatment on the expression of the HCV-induced HCC-related 186-gene signature was then assessed using digital transcript counting technology (nCounter assay) (Hoshida et al., N Engl J Med., 2008, 359(19): 1995-2004; King et al., Gut, 2014, 20. pii: gutjnl-2014-307862. doi: 10.1136/gutjnl-2014-307862). Gene Set Enrichment Analysis (GSEA) indicated that HCC high-risk genes were potently suppressed (NES: −2.29, FDR<0.001), and HCC low risk genes were significantly induced (NES: 1.73, FDR<0.001) in CLDN1-specific mAb-treated samples. Furthermore, using a computational analysis using a HCC prediction model that applies a nearest template algorithm (Hoshida et al., PLoS ONE, 2010, 5(11): e15543), the Applicants demonstrated a statistically significant reversal of the 186-gene signature in all persistently HCV-infected samples after CLDN1-specific mAb treatment (see Table 1 below).

TABLE 1

HCC prediction model showed the reversal of HCC-high risk genes following CLDN1-specific mAb.

| 10 μg/mL | | 100 μg/mL | |
|---|---|---|---|
| Sample | p-value | Sample | p-value |
| CTRL_10_3 | 0.0005 | CTRL_100_3 | 0.0005 |
| CTRL_10_2 | 0.0005 | CTRL_100_2 | 0.0005 |
| CTRL_10_1 | 0.008 | CTRL_100_1 | 0.0075 |
| CLDN1_10_2 | 0.0005 | CLDN1_100_2 | 0.004 |
| CLDN1_10_3 | 0.0005 | CLDN1_100_1 | 0.0055 |
| CLDN1_10_1 | 0.0005 | CLDN1_100_3 | 0.001 |

Huh7.5.1$^{dif}$ cells were HCV Jc1 infected. Total cellular RNA was isolated and subjected to NanoString analysis. Gene expression data was submitted to Nearest template prediction (NTP) of 186-gene-HCC risk signature in HCV infected Huh7.5.1$^{dif}$ cells treated with 10 and 100 μg/ml of CLDN1 specific mAb, analysis was performed using GenePattern. Heatmaps were obtained (data not shown). HCV-infected (Ctrl) and treated (CLDN1_10 or CLDN1_100) cells were predicted as HCC high risk and low risk. NTP statistical figures are presented below. FDR p-values < 0.05 were considered significant.

Figure 1C:
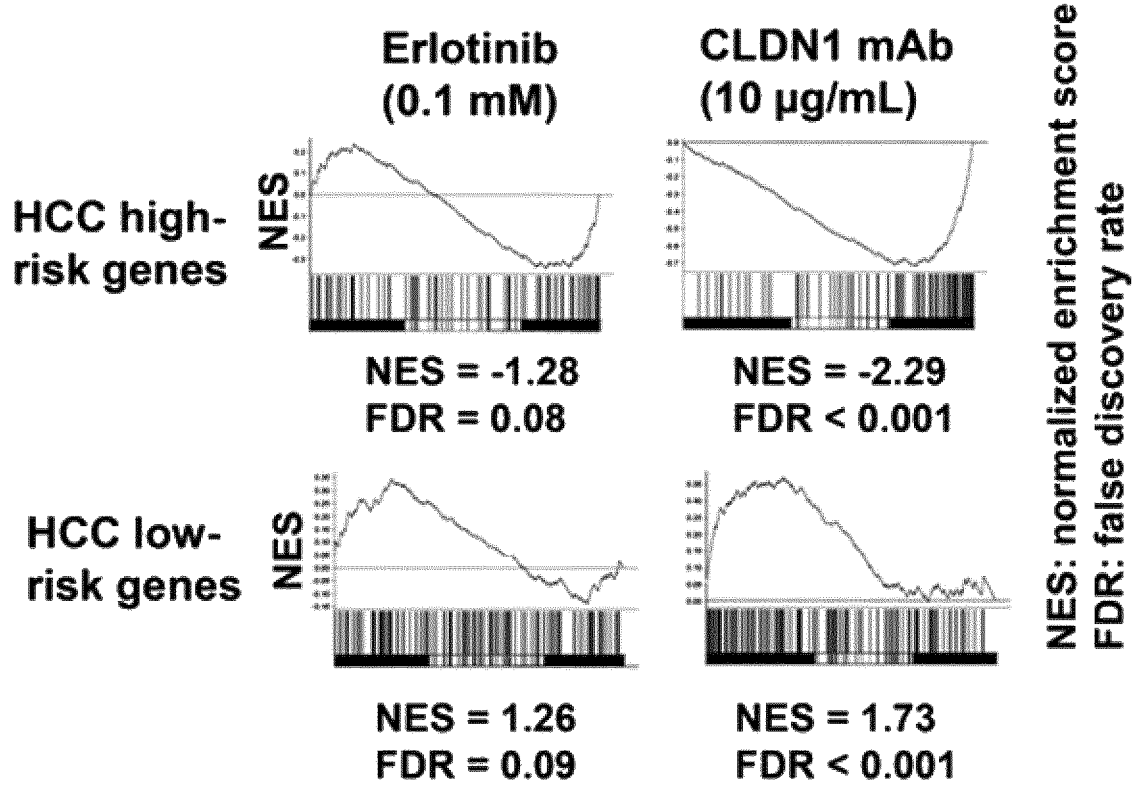

The CLDN1-specific mAb was found to reverse the 186-gene HCC risk signature in cells more potently than direct-acting antivirals and than HCC chemopreventive candidate compounds. Strikingly, the effect of the CLDN1-specific mAb was more potent than the effect of erlotinib which induced partial suppression of HCC high-risk genes (NES: −1.28, FDR=0.08) and induction of HCC low-risk genes (NES: 1.26, FDR=0.09) (see FIG. 1C).

Figure 2B:
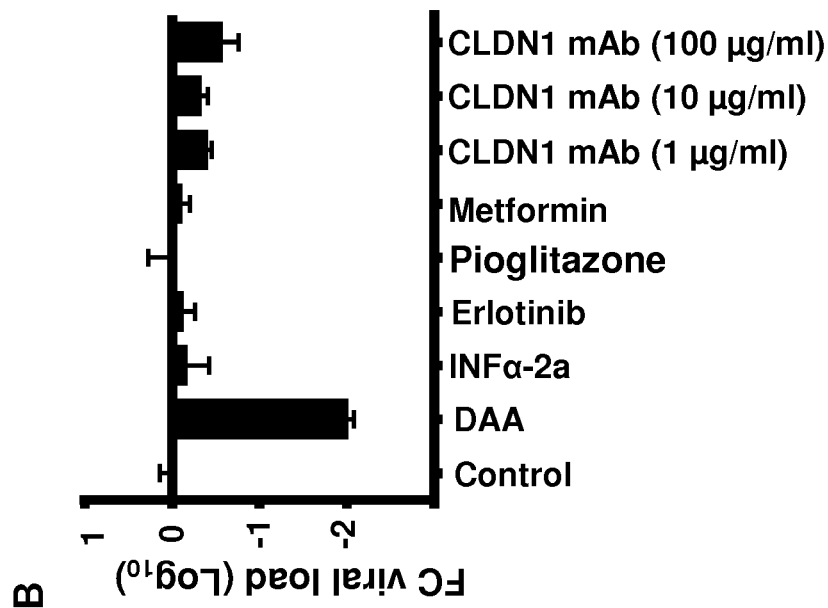
FIG. 2A-B. CLDN1-specific mAb reverses HCC high-risk genes more potently than direct-acting antivirals or other HCC chemoprevention candidate compounds independently of the viral load. A. Huh7.5.1$^{dif}$ cells were HCV Jc1 infected. On day 7 post-infection, cells were treated with different compounds. Total cellular RNA was isolated and subjected to NanoString analysis. Treatment of HCV Jc1-infected Huh7.5.1$^{dif}$ cells with DAA (1 nM DCV+1 µM SOF), interferon alpha-2a (10 IU/ml), erlotinib (0.1 µM), and pioglitazone (1 µM), partially reverses the HCC high-risk genes as shown by GSEA. Control treatment with metformin (Met, 3 μM) had no effect. Treatment with CLDN1-specific mAb (1, 10 and 100 μg/ml) potently reverses HCC-high risk genes. Heatmaps show the significance of HCC high-/low-risk gene signature induction or suppression. B. Reversal of the gene signature by CLDN1-specific mAb is independent of viral load. Relative HCV RNA expressions (normalized to GAPDH) were analyzed. HCV load in cell-based model, mean±SD, n=3. FC—Fold change, DCV—Daclatasvir, SOF—Sofosbuvir.
Figure 2A:
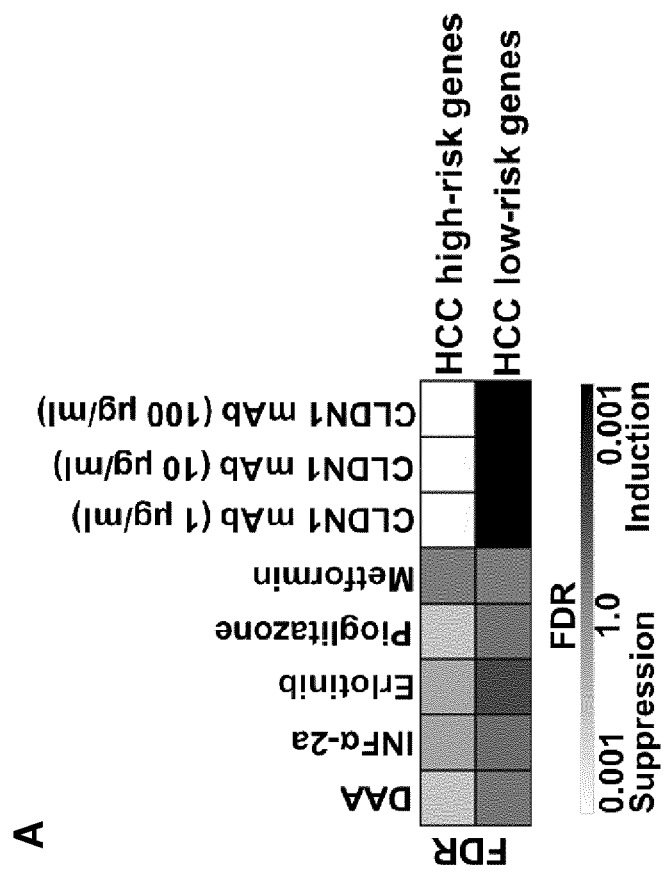

To further assess the potency of the CLDN1-specific mAb in reversing the HCC risk gene signature, the Applicants compared its effects to those of direct-acting antivirals (DAAs), interferon alpha and pioglitazone, compounds that the present Applicants have previously shown to partially suppress the HCC high-risk genes using GSEA. Metformin, a compound that was previously shown not to exhibit any effect on the HCC risk signature, was used as a negative control. The present Applicants found that the CLDN1-specific mAb reverses HCC high-risk genes more potently than the other tested compounds (see FIG. 2A). Notably, in contrast to DAAs, CLDN1-specific mAb-induced suppression of the HCC high-risk genes appeared to be independent from its effect on viral load since very low concentrations of this monoclonal antibody that do not modulate viral load in Huh7.5.1$^{dif}$ cells were potent in reversing the 186-gene signature (see FIG. 2B).

Taken together, these data indicate that the CLDN1-specific mAb potently reverses the HCC risk signature induced by HCV independently of its antiviral effect.

The CLDN1-specific mAb was found to impair EGF-MAPK signalling as a driver for hepatocarcinogenesis. The Applicants have previously shown that HCV uses EGFR and Claudin-1 as host dependency factors to enter the hepatocyte in cell culture and in vivo (Mailly et al., Clearance of persistent hepatitis C virus infection using a claudin-1-targeting monoclonal antibody, Nat Biotech, 2015, 33(5): 549-554; Lupberger et al., Hepatology, 2013, 58(4): 1225-1235; Lupberger et al., Nat Med., 2011, 17(5): 589-559; Zona et al., Cell Host Microbe, 2013, 13(3): 302-313). To assess whether HCV not only exploits EGFR and CLDN1 for entry, but also triggers intracellular signaling cascades, the present Applicants investigated virus-induced signaling in virus-infected liver cells. Taking advantage of the novel model system to study HCV disease biology (see FIG. 1), they screened the activation state of hepatocyte canonical signaling pathways, as previously described (Lupberger et al., Hepatology, 2013, 58(4): 1225-1235; Lupberger et al., Nat Med., 2011, 17(5): 589-59; Zona et al., Cell Host Microbe, 2013, 13(3): 302-313). They observed that HCV infection triggers activation of specific host signaling networks, including EGFR pathway as shown by virus-induced EGFR phosphorylation (see FIG. 3A-B), enhanced EGF and EGFR expression and significant induction of experimentally-defined EGF target gene signatures (see FIG. 3C). Interestingly, an induction of the EGF/EGFR pathway was also observed in HBV-infected as well as in ethanol-treated cells, albeit at a lower level (see FIG. 3D-E).

Figure 3F:
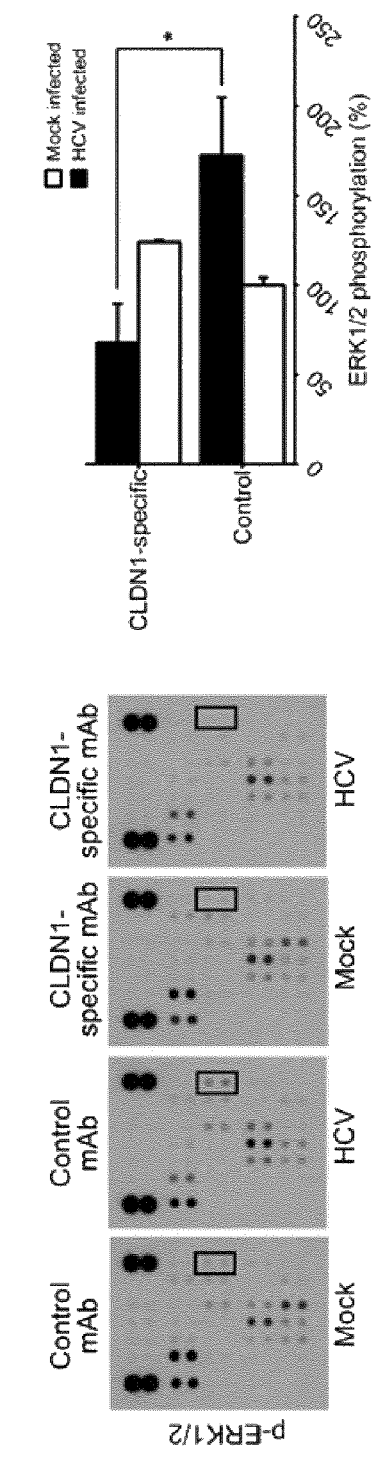
Figure 3G:
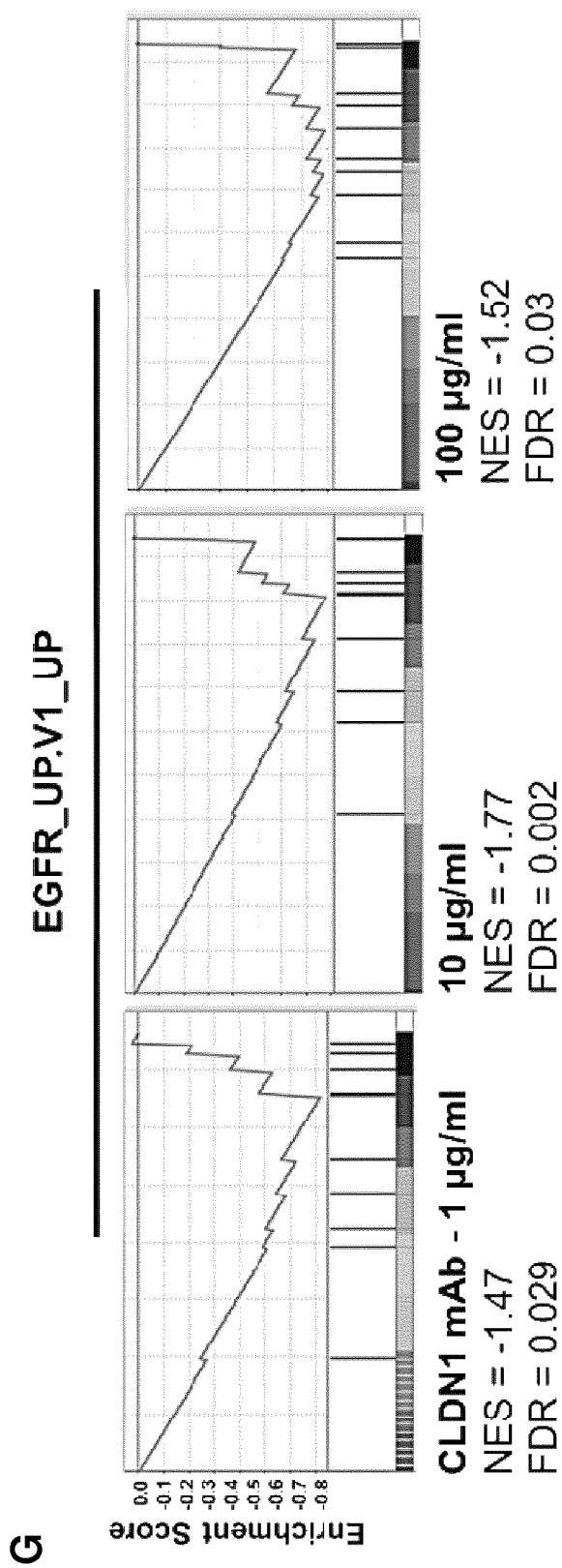
Figure 4B:
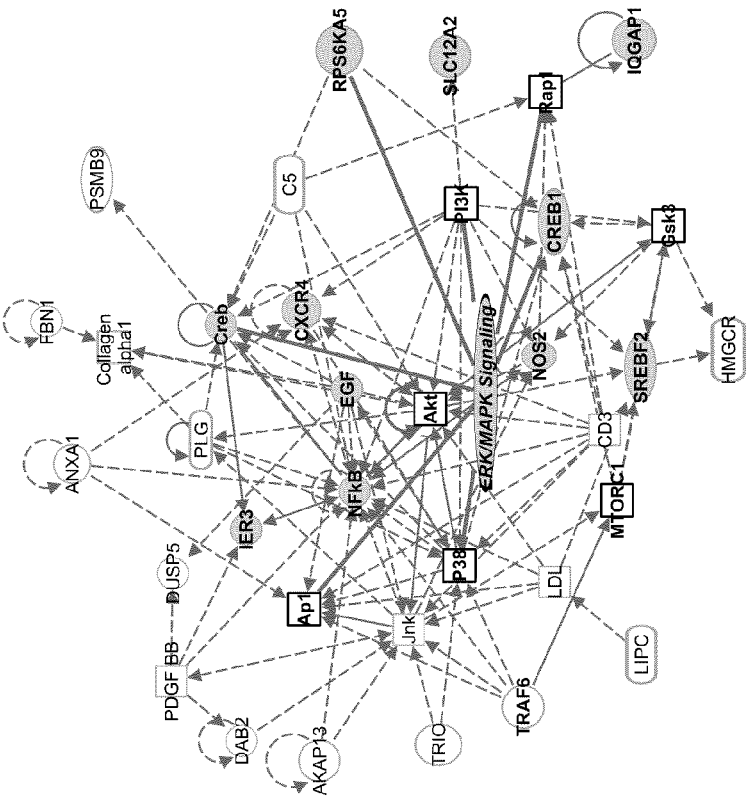
FIG. 4A-B. EGFR and MAPK signaling pathways are suppressed following CLDN1-specific mAb treatment of HCV Jc1-infected Huh7.5.1$^{dif}$ cells. In two independent experiments, Huh7.5.1$^{d1f}$ cells were HCV Jc1 infected and treated with mAbs as described above. Total cellular RNA was isolated and subjected to NanoString analysis. Differentially expressed genes were selected. Intensity expression values were normalized and log transformed; differentially expressed genes have FDR p-values <0.05 and fold change of ±1.9. Ingenuity Pathway Analysis (IPA®, webpage: qiagen.com/ingenuity) was used for the generation of network analysis. Differentially expressed genes belonging to A. EGFR and B. MAPK-signaling pathways are suppressed following CLDN1-specific mAb treatment. Filled nodes with genes in bold represent differentially expressed genes belonging to EGFR or MAPK signaling pathway, rounded rectangle meaning up-regulated and circles meaning down-regulated following CLDN1-specific mAb treatment. Squares represent predicted targets; genes in bold and black outline belong to EGFR or MAPK signaling pathway. Solid and dashed lines indicate direct and indirect interactions, respectively.
Figure 4A:
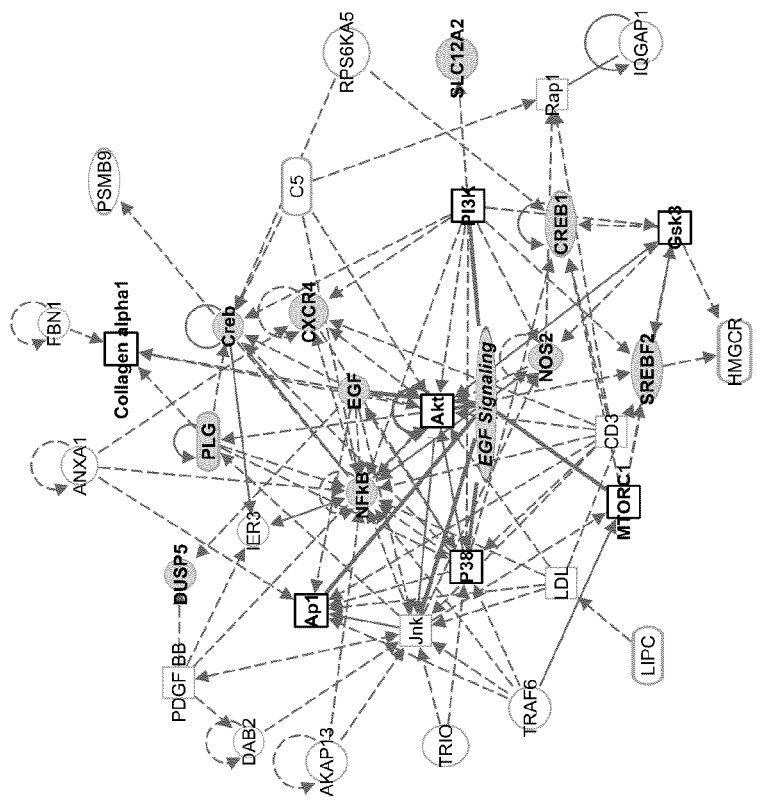

Analysis of downstream signaling pathways revealed HCV-induced phosphorylation of extracellular signal-regulated kinase (ERK) (see FIG. 3F). Since the EGFR pathway has been identified to be strongly associated with hepatocarcinogenesis in patients (Hoshida et al., N Engl J Med., 2008, 359(19):1995-2004; Hoshida et al., Gastroenterology, 2013, 144(5):1024-1030; King et al., Gut, 2014, 20. pii: gutjnl-2014-307862. doi: 10.1136/gutjnl-2014-307862; King et al., PLoS ONE, 2014, 9(12): e114747; Abu Dayyeh et al., Gastroenterology, 2011, 141(1): 141-149) and a driver for HCC in animal models (Fuchs et al., Hepatology, 2014, 59(4): 1577-1590; Lanaya et al., Nat Cell Biol., 2014, 16(10): 972-981, 1-7), it is likely that the virus-induced activation of EGFR-ERK1/2 pathways contributes to hepatocarcinogenesis. Importantly, perturbation data show that the anti-Claudin 1 mAb inhibits ERK1/2 signaling (see FIG. 3F). Significant suppression of gene expression of the EGFR pathway was also observed by analysis of the EGFR oncogenic signatures in cancer (see FIG. 3G). Single sample GSEA (ssGSEA) showed the suppression of EGFR signaling and EGFR-related genes even at low doses of the CLDN1-specific antibody (data not shown). The involvement of the EGFR pathway was further supported by network analysis of differentially expressed genes showing the suppression of EGFR (see FIG. 4A) and MAPK signaling pathways (see FIG. 4B).

Figure 5:
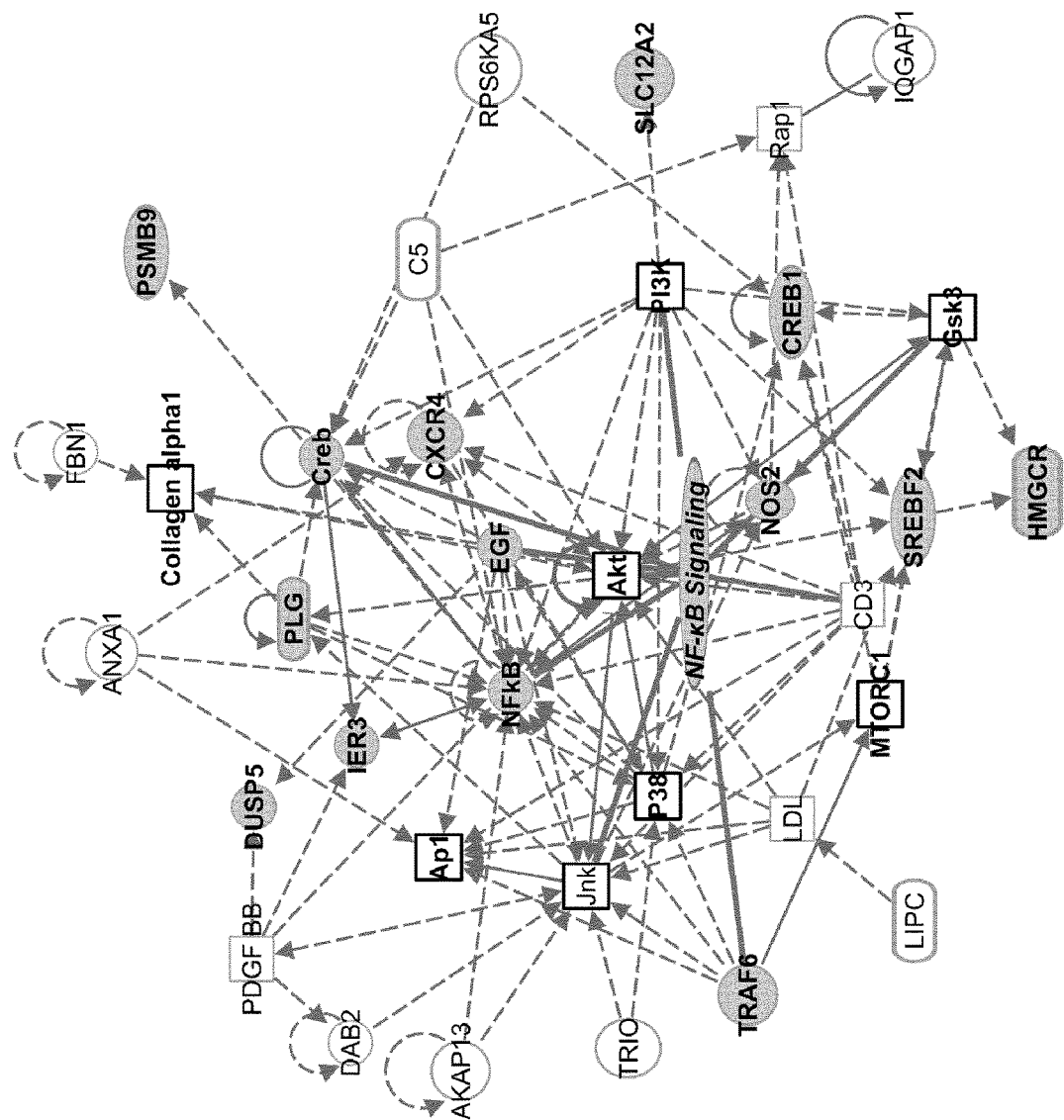
FIG. 5. CLDN1-specific mAb treatment modulates NF-κB inflammatory signaling pathway in HCV Jc1-infected Huh7.5.1$^{dif}$ cells. In two independent experiments, Huh7.5.1$^{dif}$ cells were HCV Jc1 infected and treated with mAbs as described above. Total cellular RNA was isolated and subjected to NanoString analysis. Differentially expressed genes were selected. The networks were generated through the use of Ingenuity Pathway Analysis (IPA®, webpage: qiagen.com/ingenuity). NF-κB signaling pathway is modulated following CLDN1-specific mAb treatment. Filled nodes with genes in bold represent differentially expressed genes belonging to NF-κB signaling pathway, rounded rectangle meaning up-regulated and circles meaning down-regulated following CLDN1-specific mAb treatment. Squares represent predicted targets; genes in bold and black outline belong to NF-κB signaling pathway. Solid and dashed lines indicate direct and indirect interactions, respectively.

The CLDN1-specific mAb was found to impair expression of genes related to liver disease as well as inflammatory response genes which are drivers of hepatocarcinogenesis. Furthermore, functional enrichment analysis of differentially expressed genes showed that inflammatory responses genes, including NF-κB, EBV, LMP1, MyD88 and TLR signaling, were down-regulated as shown in part A of Table 2 below) and FIG. 5, while the expression of genes involved in metastatic pathways was up-regulated (see part B of Table 2 below).

TABLE 2

CLDN1-specific mAb treatment suppresses inflammatory-related genes and induces metabolic-related genes.

| | p-value | FDR q-value |
|---|---|---|
| A. Pathways of down-regulated genes | | |
| Induction of NFkB and MAP kinases | 8.75E−05 | 2.02E−02 |
| MyD88 dependent cascade | 9.81E−05 | 2.02E−02 |
| Toll Like Receptor 7/8 (TLR7/8) Cascade | 9.81E−05 | 2.02E−02 |
| Toll Like Receptor 9 (TLR9) Cascade | 1.22E−04 | 2.02E−02 |
| Toll Like Receptor 3 (TLR3) Cascade | 1.83E−04 | 2.02E−02 |
| EBV LMP1 signaling | 2.24E−04 | 2.16E−02 |
| CREB phosphorylation | 6.11E−04 | 4.28E−02 |
| B. Pathways of up-regulated genes | | |
| Respiratory electron transport | 5.77E−09 | 2.06E−06 |
| The citric acid (TCA) cycle | 7.50E−09 | 2.06E−06 |
| Metabolism of proteins | 1.11E−05 | 5.57E−04 |
| Regulation of complement cascade | 3.01E−04 | 1.10E−02 |

TABLE 2-continued

CLDN1-specific mAb treatment suppresses inflammatory-
related genes and induces metabolic-related genes.

|  | p-value | FDR q-value |
|---|---|---|
| Proteasome Complex | 6.23E−04 | 2.14E−02 |
| Purine nucleotide salvage | 1.66E−03 | 4.14E−02 |
| Purine nucleotides de novo biosynthesis | 1.66E−03 | 4.14E−02 |

Huh7.5.1$^{dif}$ cells were HCV Jc1 infected. Following isolation of total RNA there were subjected to NanoString analysis. Intensity expression values were normalized and log transformed. Differentially expressed genes have FDR p-values < 0.05 and fold change of ±1.9. Pathway analysis was performed using ToppGene Suite A. Down-regulated genes belong to MAPK, NF-κB, and Toll-like receptor signaling, while B. up-regulated genes belong to metabolism-related pathways.

Figure 6:
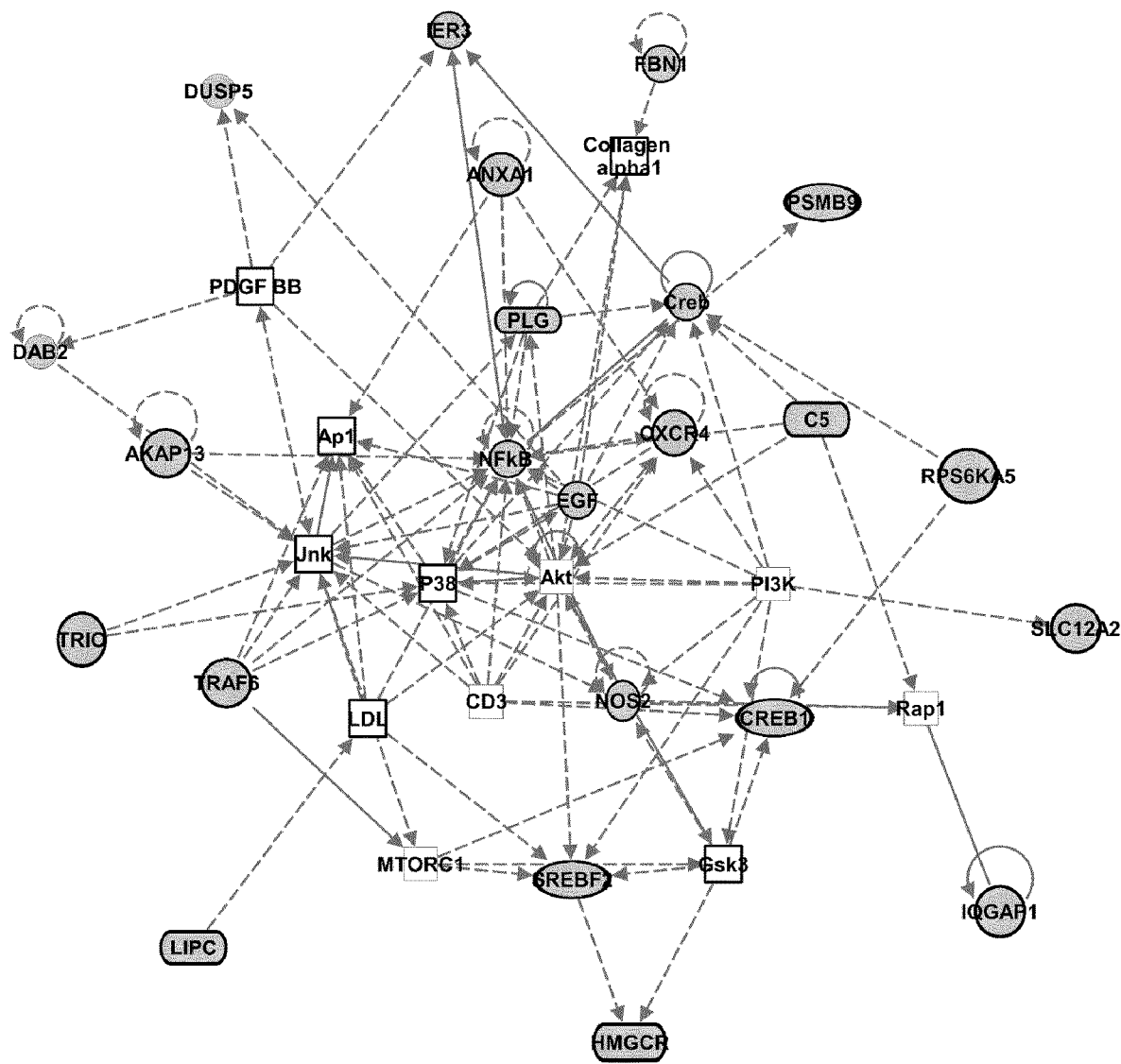
FIG. 6. Treatment of HCV Jc1-infected Huh7.5.1$^{dif}$ cells with CLDN1-specific mAb suppresses liver disease-induced genes. In two independent experiments, Huh7.5.1$^{dif}$ cells were HCV Jc1 infected and treated with mAbs as described above. Total cellular RNA was isolated and subjected to NanoString analysis. Differentially expressed genes were selected. Ingenuity Pathway Analysis (IPA®, webpage: qiagen.com/ingenuity) was used for the generation of network analysis. Liver disease-induced genes extracted by IPA software based on Ingenuity Knowledge Base are shown to be suppressed following CLDN1-specific mAb treatment. Nodes represent differentially expressed genes, rounded rectangle meaning up-regulated and circles meaning down-regulated following CLDN1-specific mAb treatment. Squares represent predicted targets. Solid and dashed lines indicate direct and indirect interactions, respectively. Genes with black outline are involved in liver diseases curated in IPA Knowledge Base.

Interestingly, eight (8) of the nine (9) genes that were previously shown to be induced by different HCC drivers, including HCV, HBV or ethanol treatment (see Bandiera et al., "A cell-based model unravels drivers for hepatocarcinogenesis and target for clinical chemoprevention", which was submitted to Nature Medicine for publication on Mar. 12, 2015 by the Applicants), were suppressed following CLDN1-specific mAb treatment (see Table 3 below). Finally, the present Applicants showed that the Claudin-1 specific antibody suppresses expression of genes involved in liver diseases (see FIG. 6).

TABLE 3

CLDN1-specific mAb treatment down-regulates genes
commonly induced by different HCC drivers including
HCV and HBV infection and ethanol treatment.

| Gene Symbol | Gene Name | FDR p-value | Fold changes |
|---|---|---|---|
| ANXA3 | Annexin A3 | 0.001 | −1.92 |
| FILIP1L | Filamin A interacting protein 1-like | 0.0014 | −1.92 |
| DUSP5 | Dual specificity phosphatase 5 | 0.002 | −1.94 |
| ANXA1 | Annexin A1 | 0.005 | −1.93 |
| EGF | Epidermal growth factor | 0.005 | −1.94 |
| SLC12A2 | Solute carrier family 12 (sodium/potassium/chloride transporter), member 2 | 0.006 | −1.95 |
| PODXL | Podocalyxin-like | 0.022 | −1.95 |
| LOXL2 | Lysyl oxidase-like 2 | 0.036 | −1.93 |

Statistical figures, FDR p-values < 0.05 were considered significant.

Collectively, these data indicate that the CLDN1-specific mAb reverses the risk for hepatocarcinogenesis, likely by impairing EGF-MAPK signaling and expression of inflammatory response genes.

Discussion

In the present study, the Applicants have shown that CLDN1, a well characterized HCV entry factor and antiviral target to prevent and treat HCV infection, is a previously undiscovered target for HCC prevention and treatment. They demonstrated that a CLDN1-specific mAb reverses HCC high-risk genes in a liver cell-based model system where a HCC risk signature common to different etiologies was induced by persistent HCV infection. Notably, the CLDN1-specific monoclonal antibody reversed this HCC risk signature more potently than any other antivirals (direct acting anti-viral, interferon alpha) or potential HCC chemopreventive agents (erlotinib, pioglitazone) that they tested. Interestingly, the CLDN1-specific mAb was found to be able to reverse the HCC risk signature at concentrations that do not have an effect on HCV load, demonstrating that the CLDN1-specific mAb may prevent the progression of HCC independently of its effect as an antiviral agent and thus exhibit a broad HCC chemoprotective activity independently of the underlying etiology. Indeed, the present Applicants have shown that the CLDN1-specific mAb reverses the expression of 8 out of 9 genes commonly induced by different HCC etiologies with the exception of GPX2. Collectively, these data highlight the promise of CLDN1 as a target for HCC chemoprevention.

CLDN1 expression increases during HCC, in particular in cirrhotic liver patients (Stebbing et al., Oncogene, 2013, 32(41): 4871-4872) and it has been shown to contribute to epithelial-mesenchymal transition (EMT), an early step in tumor progression. The underlying molecular mechanism may involve the intracellular signaling cascades downstream of CLDN1 mainly via the activation of c-Abl-PKC-ERK1/2 axis which promotes epithelial mesenchymal transition (EMT) through the activation of MMP-2 (Suh et al., Oncogene, 2013, 32(41):4873-4882; Yoon et al., J Biol Chem., 2010, 285(1): 226-233). Indeed, in the present study, the Applicants showed that the CLDN1-specific mAb impairs EGFR/MAPK signalling (see FIG. 3F,G), a driver for hepatocarcinogenesis (Fuchs et al., Hepatology, 2014, 59(4): 1577-1590; Lanaya et al., Nat Cell Biol., 2014, 16(10): 972-981, 1-7). Complementary to these observations, the functional enrichment analysis showed that the CLDN1-specific mAb suppressed expression of pathways related to EGF (see FIG. 4A) and MAPK signalling (see FIG. 4B). Moreover, the inflammatory pathway of NF-κB was shown to be suppressed (see FIG. 5). This pathway plays an important role in aggravating liver injury by promoting inflammatory responses in fibrotic livers and promotes the progression into HCC and metastasis at a later stage (Ning et al., Hepatology, 2014, 60(5): 1607-1619; Shen et al., Hepatology, 2014, 60(6): 2065-2076; Song et al., Hepatology, 2014, 60(5): 1659-1673). Furthermore, several pathways belonging to MyD88 signaling, a major player in Toll-like receptor signaling, as well as TLR7 and 9 pathways were down-regulated after CLDN1-specific mAb treatment (see Part A of Table 1 above). Recently, these pathways were suggested to be potential HCC therapeutic targets, as they play a role in inducing inflammatory responses during HCC (Leake et al., Nat Rev Gastroenterol Hepatol., 2014, 11(9): 518; Mohamed et al., Liver Int., 2015, 64(3): 483-494).

Taking into account the ability of CLDN1-specific mAb to reverse signaling (see FIGS. 1-3) and inflammatory responses driving hepatocarcinogenesis (see FIGS. 3 to 5) (Fuchs et al., Hepatology, 2014, 59(4):1577-1590; Suh et al., Oncogene, 2013, 32(41): 4873-4882; Stebbing et al., Oncogene, 2013; 32(41):4871-4872; Song et al., Hepatology, 2014, 60(5): 1659-1673; Fortier et al., J Biol Chem., 2013, 288(16): 11555-11571) as well as suppressing the well characterized HCC risk gene signature (see FIG. 2) associated with progression of liver disease (Hoshida et al., N Engl J Med., 2008, 359(19): 1995-2004; Hoshida et al., Gastroenterology, 2013, 144(5):1024-1030; King et al., Gut, 2014, 20. pii: gutjnl-2014-307862. doi: 10.1136/gutjnl-2014-307862; King et al., PLoS ONE, 2014, 9(12): e114747; Abu Dayyeh et al., Gastroenterology, 2011, 141(1): 141-149; Fuchs et al., Hepatology, 2014, 59(4): 1577-1590), the CLDN1-specific mAb is suitable for prevention and treatment of HCC. Given its ability to reverse the HCC risk gene signature independently of the etiology and independently of its antiviral effect opens perspectives to utilise CLDN1-specific mAbs to prevent and treat HCC irrespective of the etiologic cause including patients with cured HCV infection and patients with HCC due to chronic hepatitis B virus infection, alcohol, non-alcoholic fatty liver disease (NAFLD) or autoimmue or hereditary liver disease.

Example 2

Materials and Methods

Cell Lines.

Cells from the Huh7.5.1 cell line (Zhong et al., Proc Natl Acad Sci USA, 2005, 102(26): 9294-9299) were cultured in Dulbecco's Modified Eagle Medium (DMEM) containing 1% dimethylsulfoxide (DMSO) for differentiation (Huh7.5.1$^{dif}$). NTCP-overexpressing HepG2 cells (HepG2-NTCP) were selected using puromycin and cultured in DMEM (Ni et al., Gastroenterology, 2014, 146: 1070-1083; Yan et al., eLife, 2012; 1:e00049).

HCV Infection and CLDN1-Specific mAb Treatment.

Huh7.5.1$^{dif}$ cells were plated in 6-well plates and infected with HCVcc Jc1 (genotype 2a/2a) (Pietschmann et al., PNAS USA, 2006, 103: 7408-7413; Wakita et al., Nature medicine. 2005, 11(7): 791-796). CLDN1-specific mAb or control Ab (10 μg/ml) was added at day 7 post-infection. HCV infection was assessed at day 10 by qRT-PCR of intracellular RNA as previously described (Xiaa et al., PLoS pathogens. 2014, 10(5): e1004128).

HBV Infection and CLDN1-specific mAb Treatment. HepG2-NTCP cells were plated in 12-well plates and infected with either recombinant HBV (strain ayw, genotype D) (Ladner et al., Antimicrobial agents and chemotherapy, 1997, 41(8): 1715-20) or serum-purified HBV (Habersetzer et al., Liver international: Official Journal of the International Association for the Study of the Liver, 2015, 35(1): 130-139). Human CLDN1-specific mAb or control Ab (10 μg/ml) was added for 7 days. Rat CLDN1-specific mAb or control Ab (10 μg/ml) was added for 3 days following 7 days of infection. HBV infection was assessed at day 7 or 10 post-infection by qRT-PCR quantification of HBV pregenomic RNA (pgRNA) as previously described (Verrier et al., Hepatology, 2016, 63(1): 35-48).

Ethanol Treatment.

Huh7.5.1$^{dif}$ cells were plated in 6-well plates and exposed to ethanol (40 mM) and treated with CLDN1-specific or control Ab (10 μg/ml) for 10 days. Fresh medium containing ethanol and antibodies was replenished daily (Ye et al., Drug and alcohol dependence, 2010, 112(1-2): 107-116).

Transcriptional Analyses.

See Examples 1 for details. Expression of the HCC-risk signature gene expression was analyzed using Biomark HD, high-throughput RT-PCR technology (Baker et al., Nature Med., 2012, 9(6): 541-544). The expression of EMT-regulated genes was assessed by qRT-PCR Taqman Gene Expression assays (Life Technologies, USA). Expression levels were normalized to GAPDG. Relative expression was calculated using ΔΔCt method.

Bioinformatic and Statistical Analyses.

Induction/suppression of high-risk or low-risk gene signature control was assessed through GSEA with FDR<0.25 or using enrichment scores (ES) for individual genes and normalized enrichment scores (NES) for gene sets (Subramanian et al., PNAS USA, 20005, 102(43): 15545-15550).

Metabolomics.

HCV-infected Huh7.5.1$^{dif}$ cells were treated with CLDN1-specific mAb on day 7 post-infection. On day 10 post-infection, metabolites were extracted and analyzed by mass spectrometry. Data was analyzed using MetaboAnalyst 3.0 (Xia et al., Nucleic acids Research, 2015, 43(W1): W251-W257).

Results

Figure 7A:
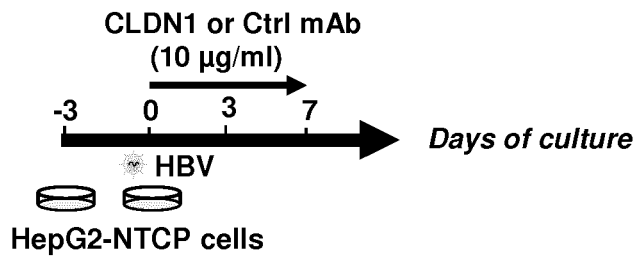
FIG. 7A-C. Patient-derived panetiology 32-gene HCC risk signature is reversed following CLDN1-specific mAb treatment in HBV-infected HepG2-NTCP cells. A. HepG2-NTCP cells were infected with serum-derived HBV and treated with human CLDN1-specific mAb or control Ab for 7 days. B. HBV infection was confirmed through quantification of relative HBV pregenomic (pg) RNA expression by qRT-PCR (mean±SD; n=3). C. Heatmap showing the suppression/induction of expression of HCC high- and low-risk genes, respectively, following human CLDN1-specific mAb treatment. Expression of the HCC-risk signature was assessed using Biomark HD, high-throughput RT-PCR technology. In scale bar, white indicates enrichment of suppression, black indicates enrichment of induction.
Figure 7B:
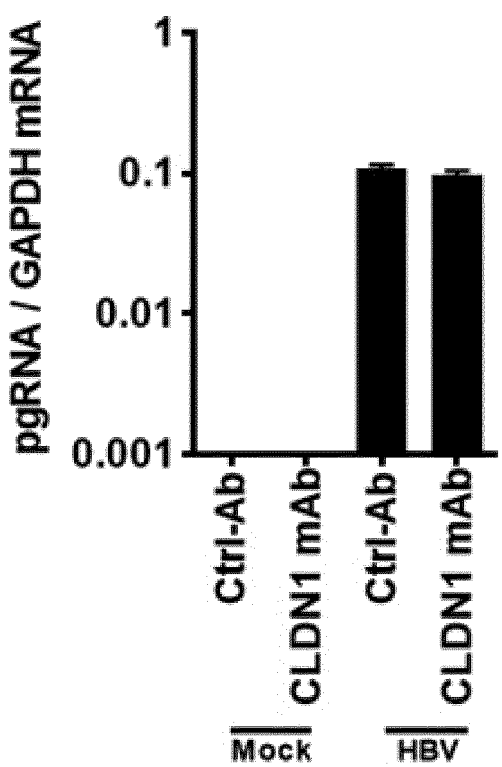
Figure 7C:
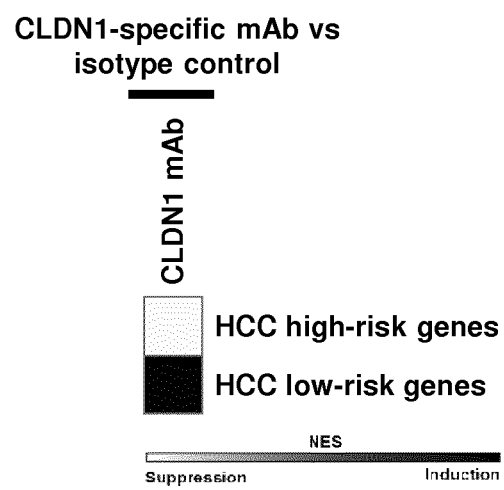

CLDN1-specific mAbs reverse the patient-derived panetiology 32-gene HCC risk signature in HBV-infected liver cell-based model. To assess the potential of the anti-CLDN1 mAbs for prevention of HCC induced by other etiologies than HCV infection, the Applicants next assessed their ability to reverse HCC-risk genes modulated by HBV infection. Recently, a 32-gene signature derived from the previously described 186-gene HCC-risk signature has been shown to have the highest significance for prediction of liver disease progression and HCC development in all major HCC etiologies (HCV, HBV, alcohol and NASH) (King et al., Gut, 2014, 64(8): 1296-1302). HepG2 liver-derived cells overexpressing NTCP, a cell entry factor for HBV, were infected with HBV and treated with human CLDN1-specific or control mAbs for 7 days (FIG. 7A). Treatment with the human CLDN1-specific mAb resulted in the induction of the HCC low-risk gene expression and suppression of the HCC high-risk genes (FIG. 7C). These results indicate that the CLDN1-specific mAbs reverse HCC-risk gene expression induced by HBV infection and suggest that the CLDN1-specific mAbs may exhibit chemopreventive activity against HBV-induced HCC.

Figures 8A, 8B:
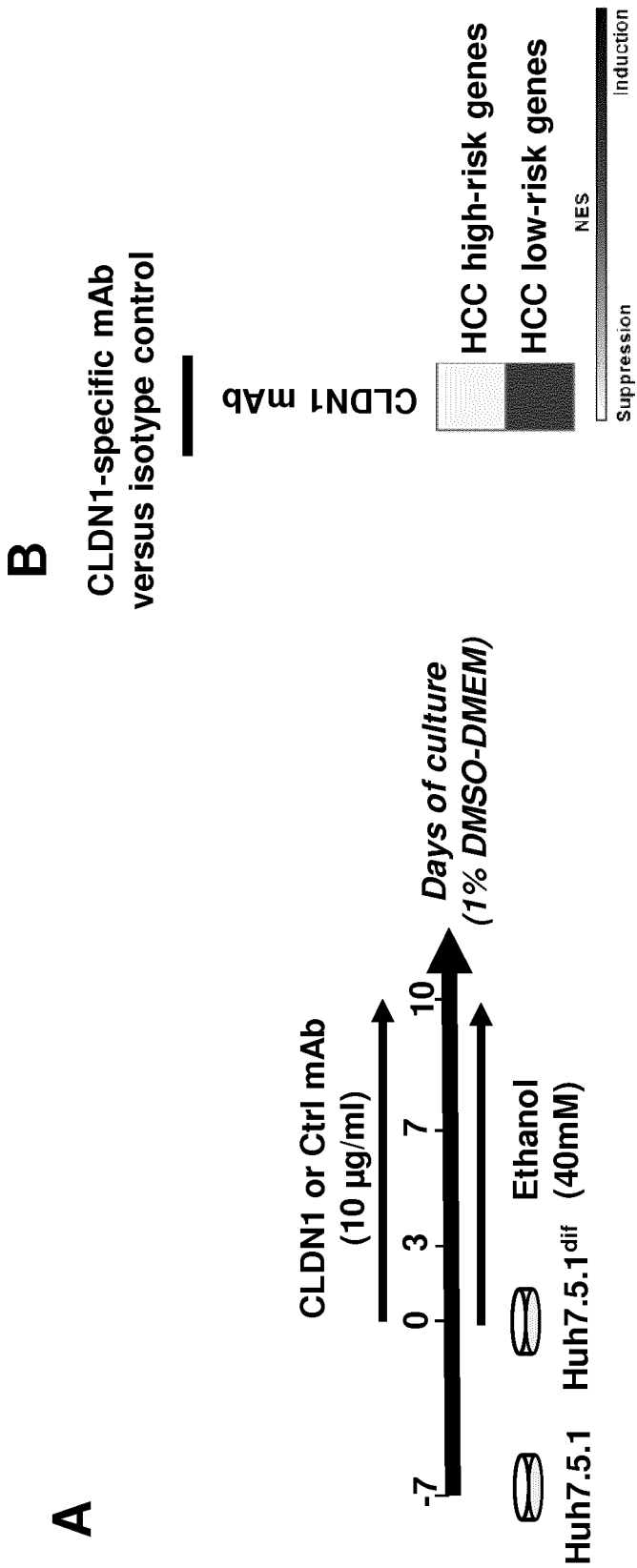
FIG. 8A-B. Patient-derived panetiology 32-gene HCC risk signature is reversed following CLDN1-specific mAb treatment in ethanol-treated liver cells. A. Huh7.5.1 cells were differentiated into hepatocyte-like Huh7.5.1$^{dif}$ cells, exposed chronically to ethanol (40 mM) and treated with human CLDN1-specific mAb or control Ab for the 10 days of exposure. B. Heatmap showing the suppression/induction of expression of HCC high- and low-risk genes, respectively, following human CLDN1-specific mAb treatment. HCC-risk signature was assessed using Biomark HD, high-throughput RT-PCR technology. In scale bar, white indicates enrichment of suppression, black indicates enrichment of induction.

CLDN1-specific mAbs reverse the patient-derived panetiology 32-gene HCC risk signature in ethanol-exposed liver cell-based model. Next, to determine the potential of the anti-CLDN1 mAb for prevention of HCC induced by alcohol consumption, the Applicants assessed the ability of the antibody to reverse HCC-risk genes modulated by a 10-day ethanol exposure of Huh7.5.1$^{dif}$ cells (FIG. 8A). They thus investigated whether the 32-gene HCC-risk signature (King et al., Gut, 2014, 64(8): 1296-1302) can be reversed in Huh7.5.1$^{dif}$ cells following treatment of ethanol-exposed cells with CLDN1-specific mAbs. Treatment with the human CLDN1-specific mAb resulted in the induction of the HCC low-risk gene expression and suppression of the HCC high-risk gene expression in ethanol-exposed cells (FIG. 8B). These results indicate that the CLDN1-specific mAbs reverse HCC-risk gene expression induced by ethanol exposure and suggest that the CLDN1-specific mAbs may exhibit chemopreventive activity against HCC induced by alcohol consumption.

Figure 9A:
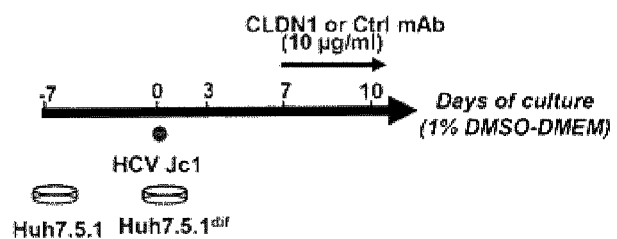
FIG. 9A-C. A Warburg-like metabolic shift associated with increased cancer risk is reversed following human CLDN1-specific mAb treatment in HCV-infected Huh7.5.1$^{dif}$ cells. A. Analysis of polar metabolites was performed in Huh7.5.1$^{dif}$ cells persistently infected with HCV. Ten days after HCV infection, metabolites were extracted and further analyzed by mass spectrometry. B. Liver cell lactate flux. Negative values: accumulation outside the cells. C. Heatmap and hierarchical clustering showing top 15 detected metabolites.
Figure 9B:
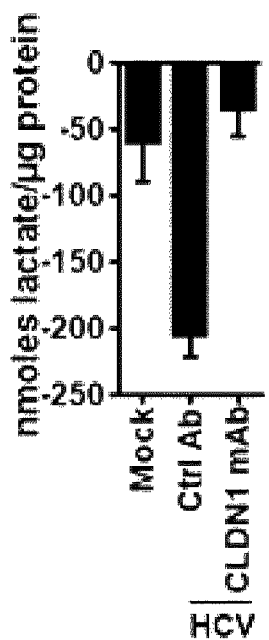
Figure 9C:
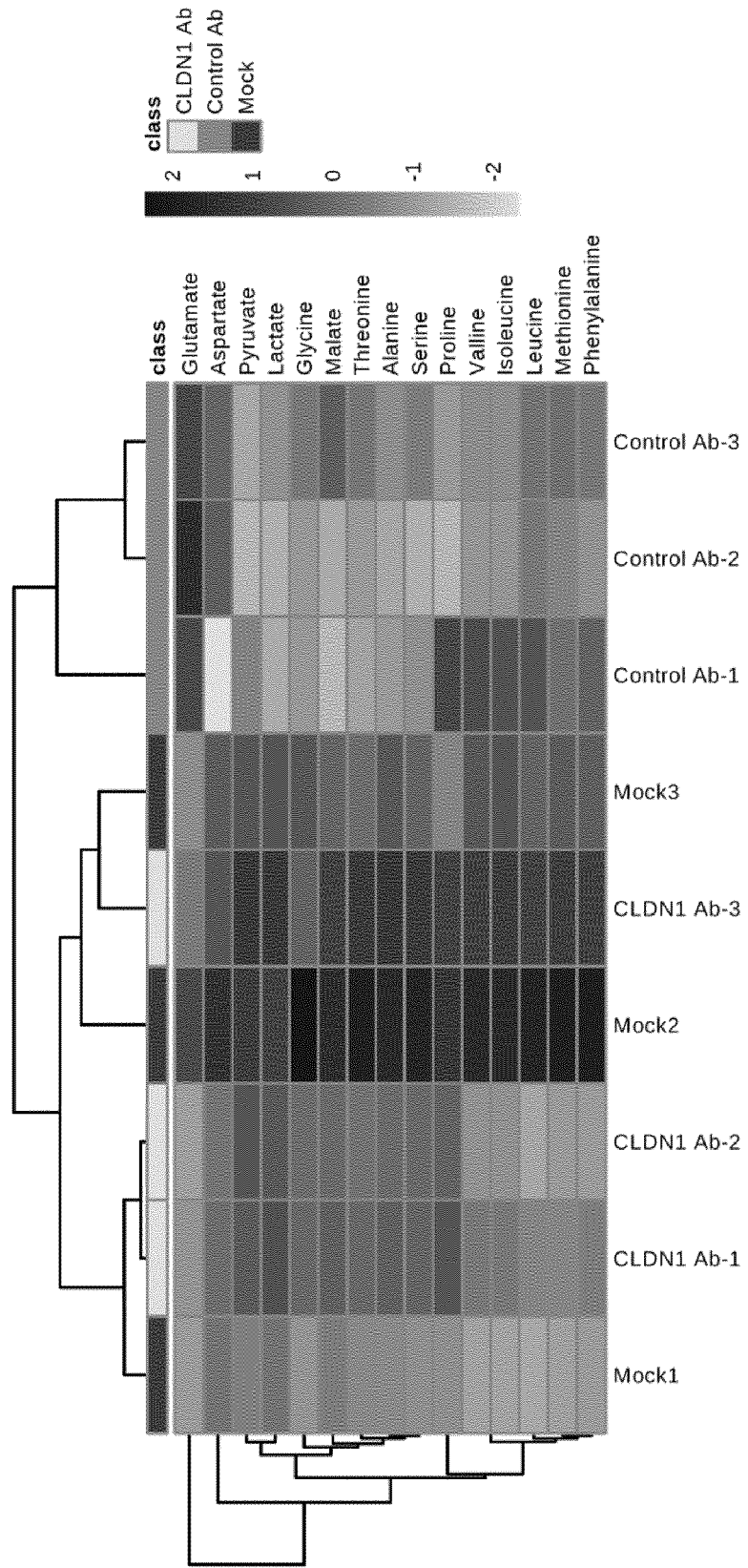

CLDN1-specific mAb reverses the Warburg-like metabolic shift associated with increased cancer risk and cancer in the liver cell-based model. Mass spectrometry-based metabolomic profiling of HCV Jc1-infected Huh7.5.1$^{dif}$ cells revealed alteration of steady-state metabolite pools in hepatocytes, including pronounced effects on lactate. Furthermore, metabolic labeling analysis demonstrated an elevation of the lactate influx into HCV Jc1-infected hepatocytes—a known Warburg-like metabolic shift associated with malignant transformation and cancer (Cantor et al., Cancer discovery, 2012, 2(10): 881-898). To assess whether the human CLDN1-specific mAb is able to reverse this metabolic shift associated with increased cancer risk and cancer, Huh7.5.1$^{dif}$ cells were chronically infected with HCV and then treated with the humanized CLDN1-specific mAb prior to metabolite analysis by mass spectrometry (FIG. 9A). The metabolic profile of the CLDN1-specific mAb-treated cells clusters with mock infected cells indicated that the humanized CLDN1-specific Ab reverses the HCV-induced metabolic shift in liver-derived cells (data not shown). Metabolic labeling analysis demonstrated that the HCV-induced lactate flux is restored to the level of the uninfected cells upon CLDN1-specific mAb treatment (FIG. 9B). Furthermore, the expressions of several metabolites belonging to the Krebs cycle were restored to their levels of expression in uninfected cells following CLDN1-specific mAb treatment of HCV-infected cells (FIG. 9C). Taken together, these data indicate that the CLDN1-specific mAb reverses the metabolic shift associated malignant transformation or cancer. This suggests that the CLDN1-specific mAb may prevent malignant transformation of hepatocytes as well as treat HCC.

Figure 10A:
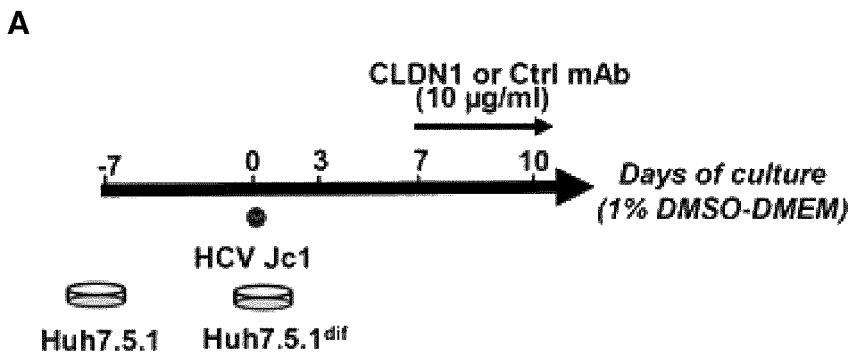
FIG. 10A-C. CLDN1-specific mAb treatment reverses epithelial to mesenchymal (EMT) transition regulators in virus-infected liver cells. A. Huh7.5.1$^{dif}$ cells were persistently infected using HCV Jc1 and treated with CLDN1-specific mAb or control Ab treatment for 3 days following 7 days of infection. B. Relative expression of Snail1 (SNAI1), Snail2 (SNAI2), and ZEB1 (ZEB1) upon CLDN1-specific mAb or control mAb treatment. C. Heatmap showing expression of genes involved in EMT. CLDN1-specific mAb treatment reversed the gene expression pattern typically observed in EMT. The genes shown belong to the 186-gene HCC-risk signature. In scale bar, white indicates enrichment of suppression, black indicates enrichment of induction. Results represent one experiment performed in triplicate. ES: Enrichment Score.
Figure 10B:
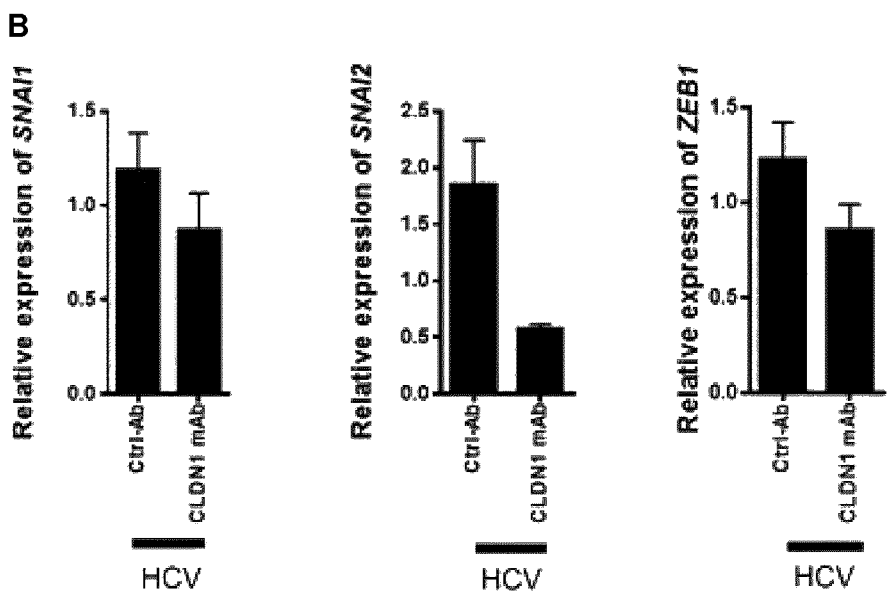
Figure 10C:
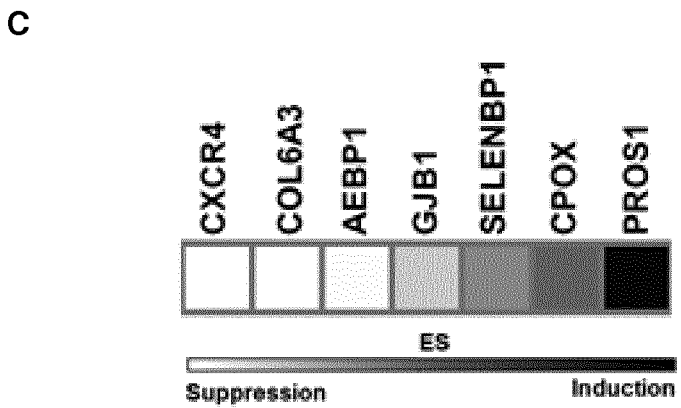

CLDN1-specific mAb treatment reverses epithelial to mesenchymal (EMT) transition regulators. EMT is an early step in metastasis, during which cancer cells lose polarity and undergo rearrangement of cytoskeletal and cell junction proteins (Lamouille et al., Nature Reviews Molecular Cell Biology, 2014, 15(3): 178-196). It is induced by transcription factors Snail, Slug and Zeb1 which have been associated with the invasiveness of the tumor (Nie et al., Oncogene, 2015, doi: 10.1038/onc.2015.428). To further study the potential of CLDN1-specific mAbs to prevent cancer development or treat HCC, the Applicants assessed the ability of the humanized CLDN1-specific mAb to modulate the expression of genes involved in EMT. Huh7.5.1$^{dif}$ cells were chronically infected with HCV Jc1 and then treated with the humanized CLDN1-specific mAb (FIG. 10A) prior to assessment of the expression of genes induced during EMT. The expression of SNAI1, SNAI2, and ZEB1 was down-regulated by the humanized CLDN1-specific mAb (FIG. 10B). Furthermore, genes belonging to the HCC 186-gene signature and dysregulated in the course of EMT (Anastassiou et al., BMC cancer. 2011; 11:529; Medici et al., Molecular Biology of the Cell, 2008, 19(11):4875-4887) were reversed upon CLDN1-specific mAb treatment (FIG. 10C). These results show that the CLDN1-specific mAb reverses the expression of genes involved in EMT suggesting that the CLDN1-specific mAb-mediated limitation of the progression of EMT could contribute to prevent the progression of HCC development as well as treat established HCC.

Conclusion

Collectively, the data presented here demonstrate that human, rat and mouse CLDN1-specific mAbs reverse the expression of genes of HCC risk signature which robustly predicts liver disease and HCC development in patients with various etiologies of HCC. The functional impact of the mAb for prevention and treatment of liver disease progression and HCC development was demonstrated by showing that mAb treatment resulted in the reduction of the expression of genes involved in EMT progression, as well as a reversal of the Warburg-like metabolic shift in liver cells associated with malignant transformation and cancer. Since the CLDN1-specific mAbs reverse the HCC-risk gene expression induced by the main causes of HCC (HCV infection, HBV infection and ethanol), the mAbs are suitable to prevent and/or treat HCC independent of its etiology including viral, metabolic and other causes.

Example 3

Figure 11D:
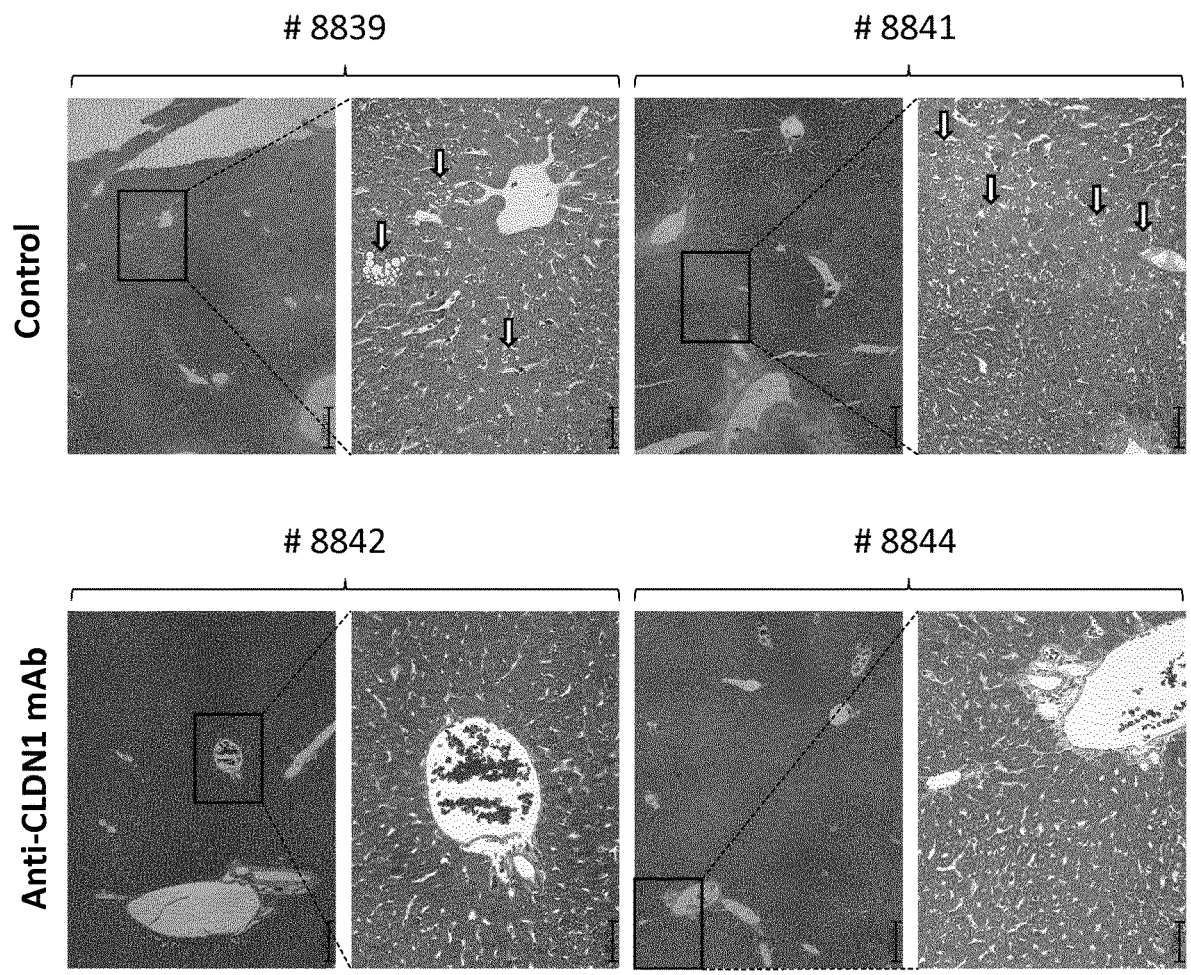

Materials and Methods 5 week-old C3H/He male mice (Janvier Labs, Saint Berthevin, France) received a single intraperitoneal injection of diethylnitrosamine (DEN, Sigma Aldrich, Saint-Quentin Fallavier, France), a well-established animal model for progressive liver disease and HCC (Frey et al., Carcinogenesis, 2000, 21: 161-166). At week 18 post-injection, two mice were sacrificed to evaluate the induction of liver disease (FIG. 11A). Between weeks 18 and 23, the remaining mice received weekly intraperitoneal injections of PBS or mouse anti-human CLDN1 mAb (20 mg/kg) for 5 weeks (FIG. 11A). One week after the fifth injection of anti-CLDN1 mAb, i.e. at week 23 post-DEN injection, all mice were sacrificed and the livers were harvested and a part was fixed in formalin for FFPE histological analysis (hematoxilin/eosin staining) as well as trichrome staining.

Results

To evaluate the effect of Claudin-1 specific mAb for prevention and treatment of progressive liver disease and HCC in vivo, the Applicants used the diethylnitrosamine (DEN) mouse model for liver disease and HCC. DEN is a carcinogenic chemical, which has been shown to robustly induce liver steatosis, fibrosis, cirrhosis and HCC in animal models. DEN models have been successfully used for proof-of-concept studies of drug treatment of liver disease progression and of HCC chemopreventive drugs (Fuchs et al., Hepatology, 2014, 59: 1577-1590; Ip et al., Cancer Prev. Res. (Phila), 2013, 6: 1304-1306; Haider et al., Mol. Cancer Ther., 2013, 12(10): 1947-1957; Park et al., J. Cell Physiol., 2012, 227(3): 899-908).

Figure 11E:
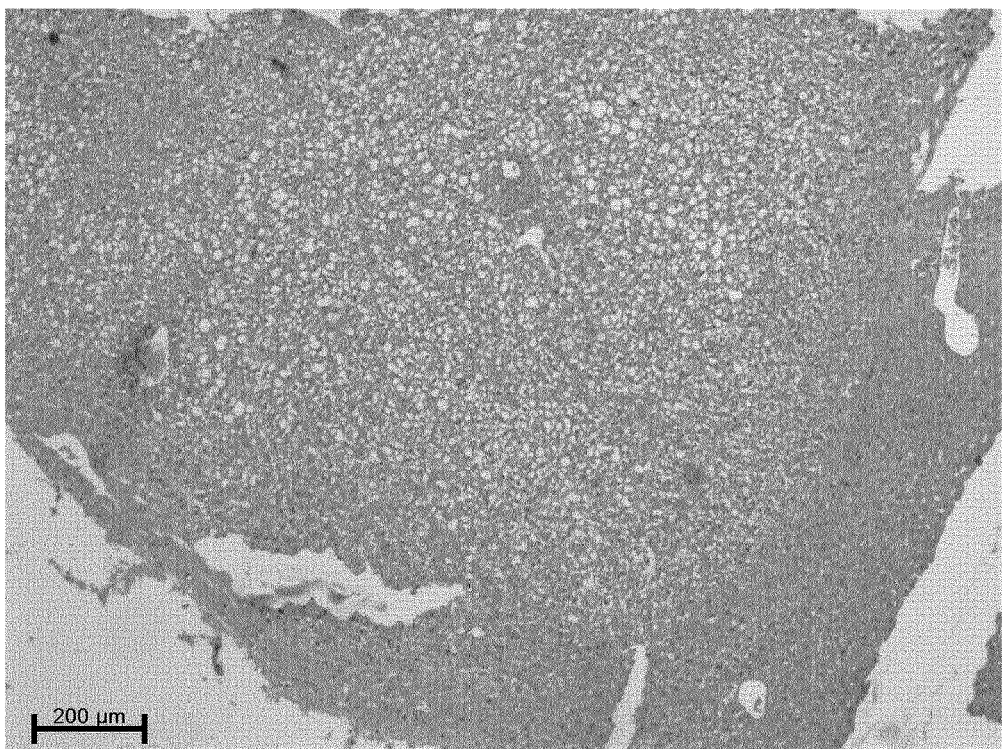
Figure 11E:
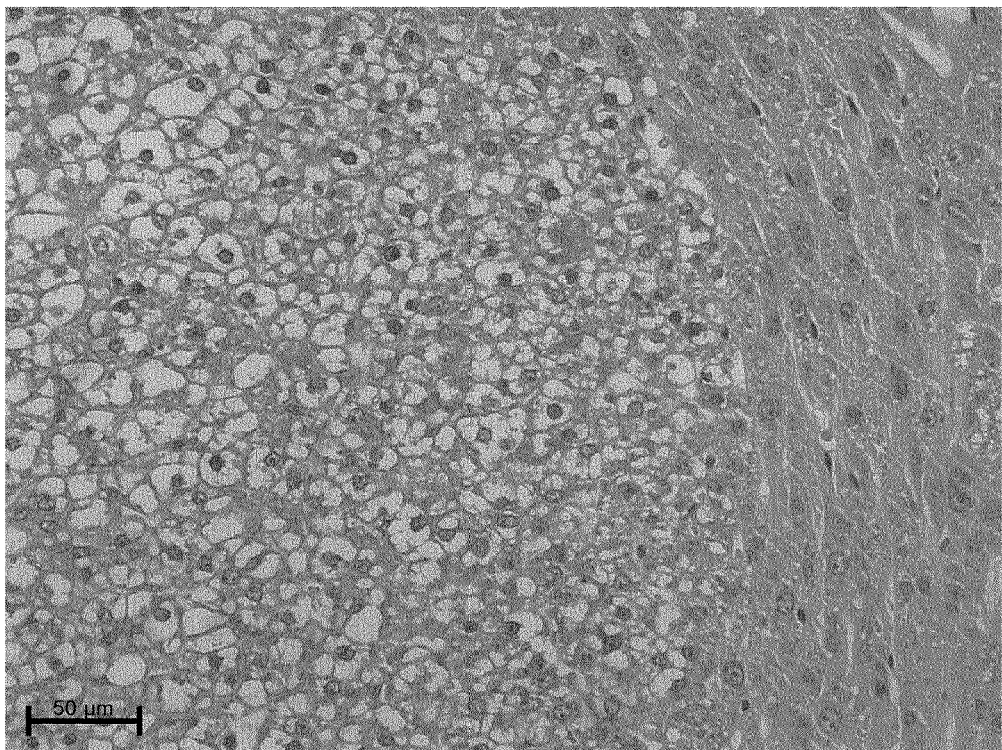

In C3H/Ha mice, a single DEN administration resulted in microvacuolar steatosis affecting around 10% of the liver as shown by histopathology analyses performed at week 18 post DEN (FIG. 11B, arrows). Liver steatosis was observed in a focal pattern and was localized predominantly periportal (FIG. 11B, left panel). Furthermore, DEN resulted in liver carcinogenesis as shown with development of a liver tumor post DEN (FIG. 11E).

The effect of the CLDN1-specific antibody on liver disease and carcinogenesis was then studied after animals had received antibody treatment for five weeks. Whereas all control animals continued to develop liver steatosis at week 23 post DEN administration, no steatosis was observed in mice having received treatment with the CLDN1-specific antibody (FIG. 11C, D). Similarly, while a tumor nodule was observed at the surface of the liver of a control mouse (mouse #8841 in FIG. 11E), no tumor was detected in any mice treated with the CLDN1-specific antibody (data not shown).

Collectively, these results demonstrate that the anti-CLDN1 mAb reverses liver steatosis, improves liver disease and provides a HCC chemopreventive effect in a state-of-the-art mouse model for progressive liver disease and HCC.

Other Embodiments

Other embodiments of the invention will be apparent to those skilled in the art from a consideration of the specification or practice of the invention disclosed herein. It is intended that the specification and examples be considered as exemplary only, with the true scope of the invention being indicated by the following claims.

What is claimed is:

1. A method for treating a non-HCV-associated hepatocellular carcinoma in a subject, said method comprising a step of administering to the subject in need thereof, an effective amount of a monoclonal anti-Claudin 1 antibody, or a biologically active fragment thereof that binds Claudin 1 extracellular domain, wherein the monoclonal anti-Claudin 1 antibody is secreted by a hybridoma cell line deposited at the DSMZ on Jul. 29, 2008 under an Accession Number selected from the group consisting of DSM ACC2931, DSM ACC2932, DSM ACC2933, DSM ACC2934, DSM ACC2935, DSM ACC2936, DSM ACC2937, and DSM ACC2938, or wherein the monoclonal antibody has the six complementary determining regions (CDRs) of a monoclonal antibody secreted by one of said hybridoma cell lines.

2. The method according to claim 1, wherein the subject has never been infected with HCV or has been cured from HCV infection.

3. The method according to claim 1, wherein the non-HCV-associated hepatocellular carcinoma is associated with hepatitis B virus (HVB) infection, alcoholism, non-alcoholic fatty liver disease (NAFLD), hereditary hemochromatosis, alpha 1 antitrypsin deficiency, *porphyria* cutanea *tarda*, Wilson's disease, tyrosinemia, glycogen storage diseases, autoimmune hepatitis, primary biliary cirrhosis, or exposure to aflatoxins, or wherein the non-HCV-associated hepatocellular carcinoma is of unknown origin.

4. The method according to claim 1, wherein the antibody is humanized, de-immunized or chimeric.

5. The method according to claim 1, wherein the biologically active fragment interferes with liver cell signalling and reverses a patient-derived HCC risk signature.

6. The method according to claim 1, wherein the biologically active fragment that binds Claudin-1 extracellular domain is a Fab fragment, a F(ab')$_2$ fragment or a Fv fragment of said monoclonal anti-Claudin 1 antibody.

\* \* \* \* \*